United States Patent
Qian et al.

(10) Patent No.: US 12,024,721 B2
(45) Date of Patent: Jul. 2, 2024

(54) METHOD OF DIFFERENTIATING HUMAN PLURIPOTENT STEM CELLS TO PODOCYTES

(71) Applicant: Wisconsin Alumni Research Foundation, Madison, WI (US)

(72) Inventors: Tongcheng Qian, Madison, WI (US); Sean P. Palecek, Verona, WI (US); Eric V. Shusta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 342 days.

(21) Appl. No.: 16/105,397

(22) Filed: Aug. 20, 2018

(65) Prior Publication Data

US 2019/0055520 A1 Feb. 21, 2019

Related U.S. Application Data

(60) Provisional application No. 62/547,347, filed on Aug. 18, 2017.

(51) Int. Cl.
*C12N 5/00* (2006.01)
*C12N 5/071* (2010.01)

(52) U.S. Cl.
CPC ......... *C12N 5/0687* (2013.01); *C12N 5/0686* (2013.01); *C12N 2500/34* (2013.01); *C12N 2500/38* (2013.01); *C12N 2500/44* (2013.01); *C12N 2500/99* (2013.01); *C12N 2501/115* (2013.01); *C12N 2501/155* (2013.01); *C12N 2501/33* (2013.01); *C12N 2501/385* (2013.01); *C12N 2501/415* (2013.01); *C12N 2501/71* (2013.01); *C12N 2506/02* (2013.01); *C12N 2506/03* (2013.01); *C12N 2506/45* (2013.01)

(58) Field of Classification Search
CPC .............. C12N 5/0687; C12N 2506/02; C12N 2506/45
See application file for complete search history.

(56) References Cited

U.S. PATENT DOCUMENTS

| | | | | |
|---|---|---|---|---|
| 2016/0137985 A1* | 5/2016 | Osafune | ................... | A61P 13/12 424/93.7 |
| 2016/0143949 A1 | 5/2016 | Ingber | | |
| 2016/0145578 A1 | 5/2016 | Bailly | | |
| 2016/0304838 A1* | 10/2016 | Nishinakamura | .... | C12N 5/0672 |
| 2020/0339957 A1* | 10/2020 | Takasato | .............. | C12N 5/0696 |

OTHER PUBLICATIONS

Cell Applications, Inc webpage. https://www.cellapplications.com/endothelial-cell-media, printed Jan. 11, 2022, pp. 1-3 (Year: 2022).*
EndoGo XF medium printout from webpage. https://www.sartorius.com/shop/ww/en/usd/applications-laboratory-cell-culture-cell-cultivation/endogo%e2%84%a2-xf-medium/p/05-400-1A?gclid=Cj0KCQiA8vSOBhCkARIsAGdp6RRavZRomGzKoTZrjmpdYkT HJR0r1qCHORuNC-X-oe2ZoEHPFYsQrYQaAog-EALw_wcB. Printed Jan. 11, 2022, pp. 1-5 (Year: 2022).*
Human Endothelial-SFM sheet. pp. 1-2. 2013 (Year: 2013).*
Serra, M., et al., Process engineering of human pluripotent stem cells for clinical application. Trends in biotechnology 30, 350-359 (2012).
Shankland, S., et al., Podocytes in culture: past, present, and future. Kidney international 72, 26-36 (2007).
Sharmin, S. et al. Human induced pluripotent stem cell-derived podocytes mature into vascularized glomeruli upon experimental transplantation. Journal of the American Society of Nephrology, ASN. 2015010096 (2015).
Song, B. et al. The directed differentiation of human iPS cells into kidney podocytes. PloS one 7, e46453 (2012).
Susztak, K., et al., Glucose-induced reactive oxygen species cause apoptosis of podocytes and podocyte depletion at the onset of diabetic nephropathy. Diabetes 55, 225-233 (2006).
Taguchi, A. et al. Higher-Order Kidney Organogenesis from Pluripotent Stem Cells. Cell stem cell 21, 730-746. e736 (2017).
Taguchi, A. et al. Redefining the in vivo origin of metanephric nephron progenitors enables generation of complex kidney structures from pluripotent stem cells. Cell stem cell 14, 53-67 (2014).
Takasato, M. et al. Directing human embryonic stem cell differentiation towards a renal lineage generates a self-organizing kidney. Nature cell biology 16, 118-126 (2014).
Takasato, M. et al. Kidney organoids from human iPS cells contain multiple lineages and model human nephrogenesis. Nature 526, 564-568 (2015).
Thomson, J. A. et al. Embryonic stem cell lines derived from human blastocysts. science 282, 1145-1147 (1998).
Vieira, A.F. et al., and the journey to cancer metastasis. Molecular cancer 14, 178 (2015).
Wharram, B.L. et al. Podocyte depletion causes glomerulosclerosis: Diphtheria toxin-induced podocyte depletion in rats expressing human diphtheria toxin receptor transgene. Journal of the American Society of Nephrology 16, 2941-2952 (2005).
Wiggins, R.-C. The spectrum of podocytopathies: a unifying view of glomerular diseases. Kidney international 71, 1205-1214 (2007).
Wilson, C.B. et al., Goodpasture's syndrome associated with influenza A2 virus infection. Ann Intern Med 76, 91-94 (1972).
Xia, Y. et al. Directed differentiation of human pluripotent cells to ureteric bud kidney progenitor-like cells. Nature cell biology 15, 1507-1515 (2013).
Xia, Y. et al. The generation of kidney organoids by differentiation of human pluripotent cells to ureteric bud progenitor-like cells. Nature protocols 9, 2693-2704 (2014).
Xinaris, C. et al. Functional human podocytes generated in organoids from amniotic fluid stem cells. Journal of the American Society of Nephrology, ASN. 2015030316 (2015).

(Continued)

*Primary Examiner* — Marcia S Noble
(74) *Attorney, Agent, or Firm* — McDonnell Boehnen Hulbert & Berghoff

(57) ABSTRACT

The present invention provides methods and kits for differentiating podocytes from pluripotent stem cells and from other cell types.

5 Claims, 12 Drawing Sheets
(11 of 12 Drawing Sheet(s) Filed in Color)
Specification includes a Sequence Listing.

(56) References Cited

OTHER PUBLICATIONS

Yanagida-Asanuma, E. et al. Synaptopodin protects against proteinuria by disrupting Cdc42: IRSp53: Mena signaling complexes in kidney podocytes. The American journal of pathology 171, 415-427 (2007).
Yu, J. et al. Human induced pluripotent stem cells free of vector and transgene sequences. Science 324, 797-801 (2009).
Yu, J. et al. Induced pluripotent stem cell lines derived from human somatic cells. Science 318, 1917-1920 (2007).
Baba, Y. et al. Constitutively active β-catenin confers multilineage differentiation potential on lymphoid and myeloid progenitors Immunity 23, 599-609 (2005).
Barisoni, L., et al., The Dysregulated Podocyte Phenotype a Novel Concept in the Pathogenesis of Collapsing Idiopathic Focal Segmental Glomerulosclerosis and HIV-Associated Nephropathy. Journal of the American Society of Nephrology 10, 51-61 (1999).
Baylis, C., et al., Chronic blockade of nitric oxide synthesis in the rat produces systemic hypertension and glomerular damage. Journal of Clinical Investigation 90, 278 (1992).
Boute, N. et al. NPHS2, encoding the glomerular protein podocin, is mutated in autosomal recessive steroid-resistant nephrotic syndrome. Nature genetics 24, 349-354 (2000).
Burrow, C.R. Regulatory molecules in kidney development. Pediatric nephrology 14, 240-253 (2000).
Carson, J. M. et al. Podocytes degrade endocytosed albumin primarily in lysosomes. PLoS One 9, e99771 (2014).
Chen, H.-F. et al. Surface marker epithelial cell adhesion molecule and E-cadherin facilitate the identification and selection of induced pluripotent stem cells. Stem Cell Reviews and Reports 7, 722-735 (2011).
Chittiprol, S., et al., Marker expression, behaviors, and responses vary in different lines of conditionally immortalized cultured podocytes. American Journal of Physiology-Renal Physiology 301, F660-F671 (2011).
Cho, Y.D. et al. Wnt3a stimulates Mepe, Matrix extracellular phosphoglycoprotein, expression directly by the activation of the canonical Wnt signaling pathway and indirectly through the stimulation of autocrine Bmp-2 expression. Journal of cellular physiology 227, 2287-2296 (2012).
Ciampi, O. et al. Generation of functional podocytes from human induced pluripotent stem cells. Stem cell research 17, 130-139 (2016).
Couser, W.G., et al., The contribution of chronic kidney disease to the global burden of major noncommunicable diseases. Kidney international 80, 1258-1270 (2011).
Das, R. et al. Transforming growth factor β1-induced apoptosis in podocytes via the extracellular signal-regulated kinase-mammalian target of rapamycin complex 1-NADPH oxidase 4 axis. Journal of Biological Chemistry 290, 30830-30842 (2015).
Duester, G. Retinoic acid synthesis and signaling during early organogenesis. Cell 134, 921-931 (2008).
Dunn, K., et al., ARPE-19, a human retinal pigment epithelial cell line with differentiated properties. Experimental eye research 62, 155-170 (1996).
Durvasula, R. V. et al. Activation of a local tissue angiotensin system in podocytes by mechanical strain. Kidney International 65, 30-39 (2004).
Foley, R.N., et al., Clinical epidemiology of cardiovascular disease in chronic renal disease. American Journal of Kidney Diseases 32, S112-S119 (1998).
Griffin, S. V., et al., Podocyte proliferation and differentiation in glomerular disease: role of cell-cycle regulatory proteins. Nephrology Dialysis Transplantation 18, vi8-vi13 (2003).
Hagen T et al Expression and characterization of GSK-3 mutants and their effect on beta-catenin phosphorylation in intact cells. J Biol Chem 277 2002 23330-5.
Haraldsson, B., et al., Properties of the glomerular barrier and mechanisms of proteinuria. Physiological reviews 88, 451-487 (2008).
Kashtan, C.E. Alport syndrome and thin glomerular basement membrane disease. Journal of the American Society of Nephrology 9, 1736-1750 (1998).
Kirouac, D. C. et al., The systematic production of cells for cell therapies. Cell stem cell 3, 369-381 (2008).
Koffler, D., et al., Immunological studies concerning the nephritis of systemic lupus erythematosus. Journal of Experimental Medicine 126, 607-624 (1967).
Kreidberg, J. A. WT1 and kidney progenitor cells. Organogenesis 6, 61-70 (2010).
Kriz, W. et al. A role for podocytes to counteract capillary wall distension. Kidney international 45, 369-376 (1994).
Kuroda, K., et al., Canonical Wnt signaling induces BMP-4 to specify slow myofibrogenesis of fetal myoblasts. Skeletal muscle 3, 5 (2013).
Lian, X. et al. Chemically defined, albumin-free human cardiomyocyte generation. Nature methods 12, 595-596 (2015).
Lian, X. et al. Robust cardiomyocyte differentiation from human pluripotent stem cells via temporal modulation of canonical Wnt signaling. Proceedings of the National Academy of Sciences 109, E1848-E1857 (2012).
Ludwig, T.E. et al. Feeder-independent culture of human embryonic stem cells. Nature methods 3, 637-646 (2006).
Mae, S. I. et al. Monitoring and robust induction of nephrogenic intermediate mesoderm from human pluripotent stem cells. Nat Commun 4, 1367, doi:10.1038/ncomms2378 (2013).
Marcelle, C., et al., Coordinate actions of BMPs, Wnts, Shh and noggin mediate patterning of the dorsal somite. Development 124, 3955-3963 (1997).
Mendelsohn, C. et al. Function of the retinoic acid receptors (RARs) during development (II). Multiple abnormalities at various stages of organogenesis in RAR double mutants. Development 120, 2749-2771 (1994).
Morizane, R. et al. Nephron organoids derived from human pluripotent stem cells model kidney development and injury. Nature biotechnology 33, 1193 (2015).
Mundel, P. et al. Rearrangements of the cytoskeleton and cell contacts induce process formation during differentiation of conditionally immortalized mouse podocyte cell lines. Experimental cell research 236, 248-258 (1997).
Musah, S. et al. Mature induced-pluripotent-stem-cell-derived human podocytes reconstitute kidney glomerular-capillary-wall function on a chip. Nature Biomedical Engineering 1, 0069 (2017).
Nangaku, M. Chronic hypoxia and tubulointerstitial injury: a final common pathway to end-stage renal failure. Journal of the American Society of Nephrology 17, 17-25 (2006).
Neugarten, J. et al., Glomerulonephritis in bacterial endocarditis. The American journal of medicine 77, 297-304 (1984).
Obara-Ishihara, T., et al., The surface ectoderm is essential for nephric duct formation in intermediate mesoderm. Development 126, 1103-1108 (1999).
Pavenstadt, H. Roles of the podocyte in glomerular function. American Journal of Physiology-Renal Physiology 278, F173-F179 (2000).
Pavenstadt, H., et al., Cell biology of the glomerular podocyte. Physiological reviews 83, 253-307 (2003).
Perantoni, A.O. "Renal development: perspectives on a Wnt-dependent process." Seminars in cell & developmental biology, vol. 14 201-208 (Elsevier, 2003).
Qian, T. et al. Directed differentiation of human pluripotent stem cells to blood-brain barrier endothelial cells. Science Advances 3, e1701679 (2017).
Radford, M.G., et al., Predicting renal outcome in IgA nephropathy. Journal of the American Society of Nephrology 8, 199-207 (1997).
Ruotsalainen, V. et al. Nephrin is specifically located at the slit diaphragm of glomerular podocytes. Proceedings of the National Academy of Sciences 96, 7962-7967 (1999).
Ryan, G.B. et al., Distribution of endogenous albumin in the rat glomerulus: role of hemodynamic factors in glomerular barrier function. Kidney international 9, 36-45 (1976).
Saleem, M.A. et al. A conditionally immortalized human podocyte cell line demonstrating nephrin and podocin expression. Journal of the American Society of Nephrology 13, 630-638 (2002).

(56) References Cited

OTHER PUBLICATIONS

Saran, R. et al. US renal data system 2016 annual data report: epidemiology of kidney disease in the United States. American journal of kidney diseases 69, A7-A8 (2017).

Sassy-Prigent, C. et al. Early glomerular macrophage recruitment in streptozotocin-induced diabetic rats. Diabetes 49, 466-475 (2000).

Schieppati, A. et al., Chronic renal diseases as a public health problem: epidemiology, social, and economic implications. Kidney International 68, S7-S10 (2005).

Schiffer, M. et al. Apoptosis in podocytes induced by TGF-β and Smad7. The Journal of clinical investigation 108, 807-816 (2001).

Schwarz, K. et al. Podocin, a raft-associated component of the glomerular slit diaphragm, interacts with CD2AP and nephrin. The Journal of clinical investigation 108, 1621-1629 (2001).

\* cited by examiner

(A)
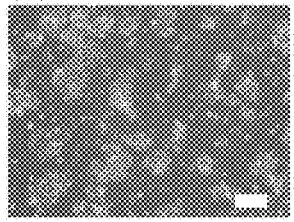
(B) 37°C-albumin                                      4°C-albumin
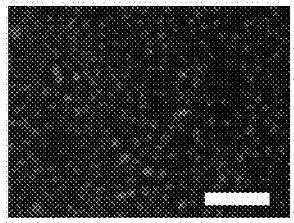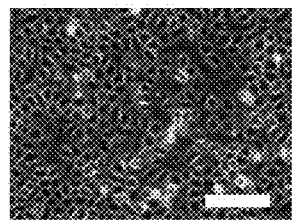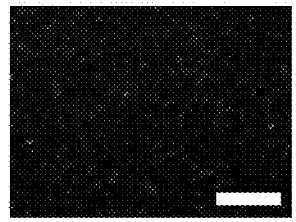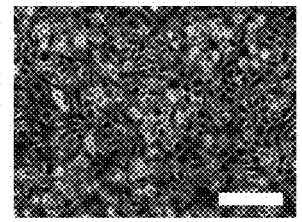
FIGS. 11A-11B

METHOD OF DIFFERENTIATING HUMAN PLURIPOTENT STEM CELLS TO PODOCYTES

CROSS-REFERENCE TO RELATED APPLICATIONS

This Application claims priority to U.S. Provisional Application No. 62/547,347 filed on Aug. 18, 2017, the contents of which are incorporated by reference in its entirety.

STATEMENT REGARDING FEDERALLY SPONSORED RESEARCH

This invention was made with government support under NS083688 and NS085351 awarded by the National Institutes of Health. The government has certain rights in the invention.

BACKGROUND OF THE INVENTION

The field of the invention relates to methods of producing human podocytes from pluripotent stem cells.

Podocytes are specialized cells that wrap around the capillaries of the glomerulus and comprise the major filtration barrier in the kidney[1]. The slit diaphragms in the glomerular filtration barrier are formed by podocyte foot processes and are mainly composed of nephrin and P-cadherin, and are associated with podocin and CD2AP[2]. The slit diaphragms serve as size-selective macromolecular sieves that retain proteins and large molecules while allowing water-soluble small molecules to pass through[3,4]. Glomerular dysfunction and associated loss of filtration capacity are the major causes of end-stage renal diseases[5-7]. Many diseases, including autoimmune diseases[8-10], bacterial endocarditis[11], HIV[12], Alport syndrome[13], diabetes[14], and hypertension[15], affect kidney function by disrupting glomerular function. In the United States, about 19.2 million people suffer from chronic kidney disease (CKD) of whom nearly 1 million are diagnosed with end-stage renal disease (ESRD)[16]. The majority of the ESRD patients are treated with dialysis instead of kidney transplantation as there is insufficient supply of transplantable organs[17].

As podocytes are terminally differentiated cells[18], obtaining sufficient populations of mature differentiated podocytes for both studying glomerular diseases or for therapeutically replacing dysfunctional podocytes has been challenging. Currently there is no replacement for dysfunctional podocytes. Immortalized human podocytes have been used to study mechanisms of glomerular diseases[18-20]. However, primary human and immortalized podocytes tend to dedifferentiate in vitro. Dedifferentiated podocytes are characterized by loss of cobblestone morphology, low synaptopodin expression, and exhibiting unstructured and dysfunctional slit diaphragms[21,22]. Animal models and primary podocytes isolated from animals are also used to study podocyte biology and glomerular diseases[23,24], but due to the species differences, these animal models fail to recapitulate the functional, structural and molecular aspects of human podocyte function[25].

Thus, an unlimited source of human podocytes exhibiting key phenotypes of healthy and diseased podocytes would be a valuable tool for advancing kidney research and treatment of CKD. Because of their unlimited self-renewal capacity and ability to differentiate into any cell type, human pluripotent stem cells (hPSCs) are a promising source of human podocytes.

SUMMARY OF THE INVENTION

The present invention provides a simple method of differentiating PSCs into PSC-derived podocyte progenitors and immature podocytes which are capable of being expanded and differentiated into mature podocytes in culture.

In one aspect, the disclosure provides a method of producing nephron progenitor cells, the method comprising: a) culturing a Brachyury$^+$ primitive streak cell population in a nephron progenitor differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into PAX2$^+$ WT1$^+$ SIX2$^+$ nephron progenitor cells.

In another aspect, the application provides a method of producing immature podocyte cells, the method comprising: a) culturing a Brachyury$^+$ primitive streak cell population in a nephron progenitor differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into PAX2$^+$ WT1$^+$ SIX2$^+$ nephron progenitor cells; and (b) culturing the PAX2$^+$ WT1$^+$ SIX2$^+$ nephron progenitor cells in podocyte differentiation medium free of exogenous Wnt/β-catenin signaling activating agent, BMPs, Activin, RA, VEGF and FGF for a time sufficient to differentiate the PAX2$^+$ WT1$^+$ SIX2$^+$ nephron progenitor cells into SIX2$^-$ immature podocyte cells that express two or more markers selected from the group consisting of PAX2, WTN1, P-cadherin, CD2AP, podocin, synaptopodin, nephrin, and ZO-1. In some aspects, at least 75% of the differentiated cells in the culture after step (b) are SIX2$^-$ immature podocyte cells.

In another aspect, the disclosure provides a method of differentiating cells into mature podocyte cells, the method comprising: a) culturing a Brachyury$^+$ primitive streak cell population in a nephron progenitor differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into PAX2$^+$ WT1$^+$ SIX2$^+$ nephron progenitor cells; (b) culturing the PAX2$^+$ WT1$^+$ SIX2$^+$ nephron progenitor cells in podocyte differentiation medium free of exogenous Wnt/β-catenin signaling activating agent, BMPs, Activin, RA, VEGF and FGF for a time sufficient to differentiate the PAX2$^+$ WT1$^+$ SIX2$^+$ nephron progenitor cells into SIX2$^-$ immature podocyte cells that express two or more markers selected from the group consisting of PAX2, WT1, P-cadherin, CD2AP, podocin, synaptopodin, nephrin, and ZO-1; and c) culturing the SIX2$^-$ immature podocyte cells in podocyte growth medium free of exogenous Wnt/β-catenin signaling activating agent, BMPs, Activin, RA, VEGF and FGF, for a time sufficient to differentiate into PAX2$^+$WT1$^+$ podocin$^+$synaptopodin$^+$ nephrin$^+$P-cadherin+CD2AP+ZO-1$^+$ mature podocyte cells. In some embodiments, the Brachyury$^+$ primitive streak cell population is obtained by differentiating pluripotent stem cells in a pluripotent stem cell differentiation medium comprising a Wnt/β-cadherin activating agent until the primitive streak cell population is obtained.

In another aspect, the disclosure provides kits for carrying out the methods described herein.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3L Wnt signaling activation alone is sufficient to differentiate hPSCs into nephron progenitor cells. (A) Schematic of podocyte differentiation factor identification. Singularized IMR90-4 hPSCs were seeded on 12-well plates coated with Matrigel®, Synthemax® or vitronectin and expanded for 3 days in mTeSR®1. Podocyte differentiation was initiated with treatment using 6 μM CHIR (CHIR99021) for 48 h in PM1 followed by treatment with different combinations of 0.1 μM or 1 μM RA, 50 ng/mL BMP7 and 50 ng/mL FGF2 from day 2 to day 6 in PM2. (B) Cells at day 6 were assessed by Western blot for the expression level of WT1. (C) Expression level was quantified via Image J. The expression was first normalized to β-actin and then compared to WT1 expression in the absence of FGF2, RA and BMP7. (D, E) Expression of phosphorylated SMAD was assessed by Western blot after cells were treated with dorsomorphin (0 μM to 10 μM) from day 1 to day 3 or from day 3 to day 4. (F, G) Expression of BMP7 at day 1 and day 2 was verified by immunofluorescence and Western blot of cell lysate. (H, I) Cells were differentiated in the presence or absence of 1 μM dorsomorphin treatment from day 1 to day 3 and at day 16 were assessed for expression of PAX2 and WT1 by flow cytometry. Data were collected from three independent replicates and are plotted as mean±SEM. *p<0.05. ***p<0.001.

FIGS. 11A-11B. Morphology and albumin uptake of human primary podocytes. (A) Morphology of primary human podocytes under standard culture conditions. (B) Confirmation of the temperature dependence endocytosis in human primary podocytes. Human primary podocytes were tested for their ability to endocytose Alexa Fluor 555-labeled albumin in a temperature-dependent manner at 37° C. and at 4° C. Endocytosis is inhibited at 4° C. in human primary podocytes, similar to the results of the iPSC-derived podocytes.

DETAILED DESCRIPTION OF THE INVENTION

Figures 1A, 1B, 1C, 1D, 1E, 1F, 1G, 1H, 1I, 1J, 1K:
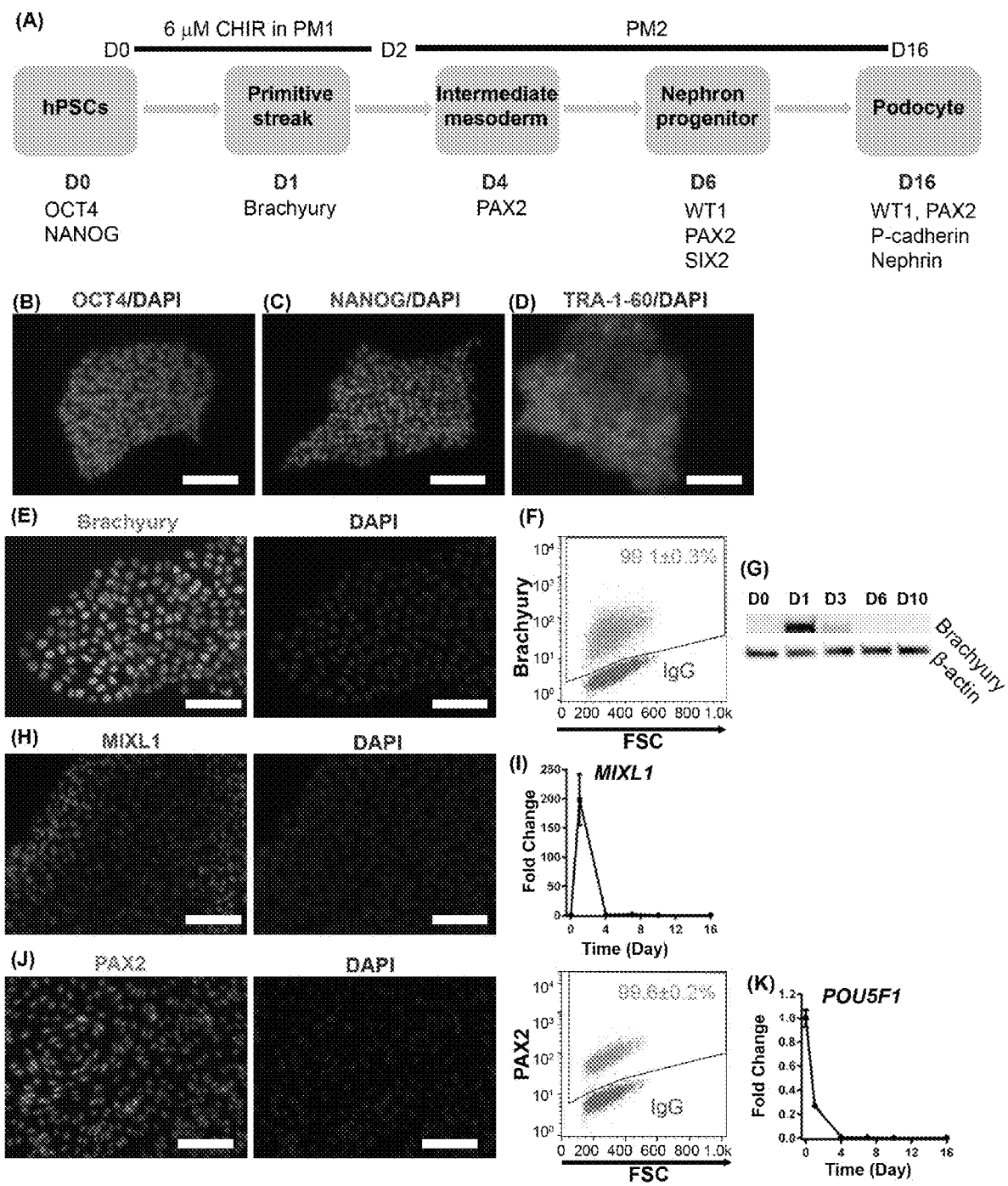
FIGS. 1A-1K. Schematic of podocyte differentiation protocol. (A) Before differentiation, singularized hPSCs were seeded on 12-well plates coated with Matrigel®, vitronectin or Synthemax® at $2 \times 10^4$ cell/cm$^2$ and expanded for 3 days in mTeSR®1. Differentiation to primitive streak was initiated by 48 hr treatment with 6 μM CHIR99201 in medium designated podocyte medium 1 (PM1). Cells progress to nephron progenitors at day 6 and eventually to mature podocyte cells in podocyte medium 2 (designated PM2) at day 16. The pluripotent state of expanded hPSCs was verified prior to differentiation by immunofluorescence for (B) OCT4, (C) NANOG and (D) TRA1-60. Expression of the primitive streak marker brachyury during differentiation was assessed by (E) immunofluorescence and (F) flow cytometry 24 hr after CHIR99201 treatment and (G) Western blot from day 0 to day 16. Expression of primitive streak marker MIXL1 during differentiation was assessed by (H) immunofluorescence. Expression levels of primitive streak gene MIXL1 (I) and the pluripotent gene POU5F1 (K) relative to the housekeeping gene GAPDH were assessed by qRT-PCR from day 0 to day 16. (J) At day 4, expression of the intermediate mesoderm marker PAX2 was verified by immunofluorescence and flow cytometry. In flow cytometry plots, red dots represent isotype control treated cells used to identify the gated regions and blue dots represent cells stained for the indicated marker. Numbers indicate the fraction of stained cells (blue) in the gated regions. Data are represented as mean±SEM of three replicates. Scale bar, 100 μm.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

In describing the embodiments and claiming the invention, the following terminology will be used in accordance with the definitions set out below.

As used herein, "about" means within 5% of a stated concentration range or within 5% of a stated time frame.

The terms "defined culture medium," "defined medium," and the like, as used herein, indicate that the identity and quantity of each medium ingredient is known.

As used herein, the terms "chemically-defined culture conditions," "fully defined, growth factor free culture conditions," and "fully-defined conditions" indicate that the identity and quantity of each medium ingredient is known and the identity and quantity of supportive surface is known.

As used herein, "effective amount" means an amount of an agent sufficient to evoke a specified cellular effect according to the present invention.

As used herein, the term "pluripotent cell" and "pluripotent stem cell" means a cell capable of differentiating into cells of all three germ layers. Examples of pluripotent cells include embryonic stem (ES) cells and induced pluripotent stem (iPS) cells. As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells.

As used herein, the term "podocytes" may refer to immature or mature podocytes that express one or more of the podocyte markers selected from the group consisting of PAX2, WT1, P-cadherin, CD2AP, podocin, synaptopodin, nephrin and ZO-1. Podocytes do not express the marker SIX2.

The term "nephron progenitor" or "podocyte progenitor" refer to cells which express the WT1, PAX2, and SIX2 markers (e.g., WT1$^+$PAX2$^+$SIX2$^+$ nephron progenitors). SIX2 is a marker specific to nephron progenitors.

The term "immature podocyte" as used herein refers to cell populations that have differentiated from nephron progenitors and express a number of the podocyte markers, including, PAX2, WT1, P-cadherin, CD2AP, podocin, synaptopodin, nephrin and ZO-1 (e.g., express two or more of the markers) but do not express the podocyte progenitor marker SIX2 (i.e., SIX$^-$). Further, the immature podocytes do not have mature podocyte morphology including formation of foot processes, and are able to differentiate in culture.

The term "mature podocytes" as used herein refers to the non-differentiating mature podocytes that have a flattened morphology characterized by long processes (also called foot projections or pedicels) which wrap around the capillaries and form slit diaphragms. These mature podocytes express the podocyte markers, including, PAX2, WT1, P-cadherin, CD2AP, podocin, synaptopodin, nephrin and ZO-1 (e.g., PAX2$^+$WT1$^+$ podocin$^+$synaptopodin$^+$nephrin$^+$ P-cadherin+CD2AP+ZO-1$^+$ mature podocytes). Mature podocytes do not express the marker SIX2.

The present disclosure relates generally to methods for producing pure population of podocytes in culture under defined conditions without a cell sorting step. This method provides a renewable source of podocytes for downstream applications. To generate podocytes (immature or mature), a primitive streak population of cells is cultured under conditions sufficient to progress to mesoderm precursors, nephron progenitors, and eventually mature into immature and mature podocytes as described herein using defined medium that does not contain exogenous growth factors (BMPs, FGFs, and VEGFs), activin or retinoic acid. Podocytes generated via the methods described herein adopt podocyte morphology, express canonical podocyte markers, and exhibit podocyte phenotypes, including albumin uptake, and TGF-β1 triggered cell death. These methods provides a simple, straightforward procedure to generate large pure populations of podocytes in vitro. A renewable supply of a pure podocytes enables in vitro disease modeling and drug screening as well as in vivo cell therapies to replace dysfunctional podocytes. This simple and novel strategy to generate both immature and mature podocytes from in vitro tissue culture cells (e.g., from PSCs or a Brachyury$^+$ primitive streak cell population derived from PSCs) allows for in vitro disease modeling and drug screening as well as in vivo cell therapies (e.g., formation of patient-specific podocytes for disease modeling and treatment).

The disclosure provides in one embodiment a method of producing nephron progenitor cells comprising a) culturing a Brachyury$^+$ primitive streak cell population in a nephron progenitor differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into PAX2$^+$ WT1$^+$ SIX2$^+$ nephron progenitor cells.

In some embodiments, the cells are cultured for a sufficient time such that at least 75% of the differentiated cells are PAX2$^+$ WT1$^+$ SIX2$^+$ nephron progenitor cells. Alternatively, the cells are cultured for a sufficient time that at least 80% of the differentiated cells are PAX2$^+$ WT1$^+$ SIX2$^+$ nephron progenitor cells, alternatively at least 85% of the differentiated cells are PAX2$^+$ WT1$^+$ SIX2$^+$ nephron progenitor cells, alternatively at least 90% of the differentiated cells are PAX2$^+$ WT1$^+$ SIX2$^+$ nephron progenitor cells, alternatively at least 95% of the differentiated cells are PAX2$^+$ WT1$^+$ SIX2$^+$ nephron progenitor cells, alternatively at least 98% of the differentiated cells are PAX2$^+$ WT1$^+$ SIX2$^+$ nephron progenitor cells, alternatively at least 99% of the differentiated cells are PAX2$^+$ WT1$^+$ SIX2$^+$ nephron progenitor cells.

In one embodiment, the sufficient amount of time for step (a) is at least about 4 days. In some embodiments, cells are cultured in step (a) for a sufficient time to form nephron progenitors, e.g., cells that express WT1, PAX2, and SIX2. Suitable time periods for culture include, but are not limited to, about 4 to about 6 days, including, about 5 days, about 6 days. Nephron progenitors at this stage can be frozen in a suitable cryopreservation medium for later thawing and use.

As described herein, "nephron progenitor differentiation medium" is medium suitable for the survival in in vitro tissue culture of nephron progenitor cells and allows for the growth and differentiation of the nephron progenitor cells from a primitive streak population. Suitable medium for use as a nephron progenitor differentiation medium are known in the art, including, for example, but not limited to, human endothelial serum-free medium (hESFM), PM2 (human endothelial serum-free medium (hESFM) and a medium supplement (e.g., 2% B-27® (Table 1, e.g., biotin, DL alpha tocopherol acetate, DL alpha-tocopherol, vitamin A (acetate), BSA, fatty acid free fraction V, catalase, human recombinant insulin, human transferrin, superoxide dismutase, corticosterone, D-galactose, ethanolamine HCl, glutathione (reduced), L-carnitine HCl, linoleic acid, linolenic acid, progesterone, putrescine 2HCl, sodium selenite and T3 (triodo-I-thyronine)). Other suitable medium may be used as long as the medium does not contain exogenous Wnt/β-catenin activating agents, exogenous growth factors, e.g., bone morphogenetic proteins (BMPs), vascular endothelial growth factor (VEGF) and fibroblast growth factor (FGF), retinoic acid and activin.

TABLE 1

| Components of B-27 ® | |
|---|---|
| Biotin | D-Galactose |
| DL Alpha Tocopherol Acetate | Ethanolamine HCl |
| DL Alpha-Tocopherol | Glutathione (reduced) |
| Vitamin A (acetate) | L-Carnitine HCl |
| BSA, fatty acid free Fraction V | Linoleic Acid |
| Catalase | Linolenic Acid |
| Human Recombinant Insulin | Progesterone |
| Human Transferrin | Putrescine 2HCl |
| Superoxide Dismutase | Sodium Selenite |
| Corticosterone | T3 (triodo-I-thyronine) |

Suitably, the nephron progenitor differentiation medium is free of any known FGF, for example, FGF 1 through 10.

The defined medium used in the methods described are free of exogeneous BMPs. Suitable BMPs include, but are not limited to, BMP 1 through 15.

In one embodiment, the defined medium used in step (a) consists essentially of a cell culture medium, e.g., human endothelial serum-free medium (hESFM) and 2% B-27®. No additional growth hormones or factors are added.

In another embodiment, a method of producing immature podocyte cells is provided. The method comprises a) culturing a Brachyury$^+$ primitive streak cell population in a nephron progenitor differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into PAX2$^+$WT1$^+$SIX2$^+$ nephron progenitor cells; and (b) culturing the PAX2$^+$WT1$^+$SIX2$^+$ nephron progenitor cells in podocyte differentiation medium free of exogenous Wnt/β-catenin signaling activating agent, BMPs, Activin, RA, VEGF and FGF for a time sufficient to differentiate the PAX2$^+$WT1$^+$SIX2$^+$ nephron progenitor cells into SIX2$^-$ immature podocyte cells that express two or more markers selected from the group consisting of PAX2, WTN1, P-cadherin, CD2AP, podocin, synaptopodin, nephrin, and ZO-1.

In some embodiments, the sufficient amount of time to complete steps (a) and (b) is at least 8 days. In some embodiments, cells are cultured in step (a) and (b) for a sufficient time to form SIX$^-$ immature progenitor cells, e.g., cells that express two or more markers selected from the group consisting of PAX2, WTN1, P-cadherin, CD2AP, podocin, synaptopodin, nephrin, and ZO-1. Suitable time periods for culture include, but are not limited to, at least 8 days, alternatively at least 9 days, alternatively at least 10 days. SIX$^-$ immune podocytes at this stage can be frozen in a suitable cryopreservation medium for later thawing and use.

"Podocyte differentiation medium" is medium suitable for the survival in in vitro tissue culture of immature podocyte cells and allow for the growth and differentiation of the immature podocyte cells. In some embodiments, the nephron progenitor medium is the same as the podocyte differentiation medium. Suitable medium for use as a podocyte differentiation medium are known in the art, including, for example, but not limited to, human endothelial serum-free medium (hESFM) (ThermoFisher Scientific), PM2 (human endothelial serum-free medium (hESFM) and a medium supplement (e.g., 2% B-27® (Table 1)). In some embodiments the podocyte differentiation medium is the same as the nephron progenitor differentiation medium. In some embodiments, the podocyte differentiation medium and nephron progenitor differentiation medium are different.

In an alternative embodiment, a method of producing immature podocytes is provided comprising (i) culturing a Brachyury+ primitive streak cell population in a podocyte differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into SIX2− immature podocyte cells that express two or more markers selected from the group consisting of PAX2, WTN1, P-cadherin, CD2AP, podocin, synaptopodin, nephrin, and ZO-1. In some embodiments, the sufficient amount of time to complete steps (i) is at least 8 days, alternatively at least 9 days, alternatively at least 10 days. SIX− immune podocyte cells at this stage can be frozen in a suitable cryopreservation medium for later thawing and use.

In another alternative embodiment, a method of producing immature podocyte cells is provided comprising (i) culturing PAX2+WT1+SIX2+ nephron progenitor cells in a podocyte differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into SIX2− immature podocyte cells that express two or more markers selected from the group consisting of PAX2, WTN1, P-cadherin, CD2AP, podocin, synaptopodin, nephrin, and ZO-1. In some embodiments, the sufficient amount of time to complete steps (i) is at least 2 days, alternatively at least 4 days, alternatively at least 6 days. SIX− immune podocyte cells at this stage can be frozen in a suitable cryopreservation medium for later thawing and use.

In some embodiments of the method of producing immature podocyte cells, at least 75% of the differentiated cells obtained in the culture are SIX2− immature podocyte cells. In some embodiments, at least 80% of the differentiated cells are SIX2− immature podocyte cells, at least 85% of the differentiated cells are SIX2− immature podocyte cells, at least 90% of the differentiated cells are SIX2− immature podocyte cells, at least 95% of the differentiated cells are SIX2− immature podocyte cells, at least 98% of the differentiated cells are SIX2− immature podocyte cells, or at least 99% of the differentiated cells are SIX2− immature podocyte cells.

In some embodiments, at least 90% of the SIX2− immature podocyte cells in culture express PAX2, WT1, P-cadherin, CD2AP, podocin, synaptopodin, nephrin, and ZO-1. In some embodiments, at least 95% of the SIX2− immature podocyte cells in culture express PAX2, WT1, P-cadherin, CD2AP, podocin, synaptopodin, nephrin, and ZO-1.

In another embodiment, the present disclosure provides methods of differentiating mature podocytes, the method comprising: a) culturing a Brachyury+ primitive streak cell population in a nephron progenitor differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into PAX2+ WT1+ SIX2+ nephron progenitor cells; (b) culturing the PAX2+WT1+SIX2+ nephron progenitor cells in podocyte differentiation medium free of exogenous Wnt/β-catenin signaling activating agent, BMPs, Activin, RA, VEGF and FGF for a time sufficient to differentiate the PAX2+WT1+SIX2+nephron progenitor cells into SIX2− immature podocyte cells that express two or more markers selected from the group consisting of PAX2, WT1, P-cadherin, CD2AP, podocin, synaptopodin, nephrin, and ZO-1; and (c) culturing the SIX2− immature podocyte cells in podocyte growth medium free of exogenous Wnt/β-catenin signaling activating agent, BMPs, Activin, RA, VEGF and FGF, for a time sufficient to differentiate into PAX2+WT1+podocin+synaptopodin+nephrin+P-cadherin+CD2AP+ZO-1+ mature podocyte cells. The mature podocyte cells can be characterized by losing expression of SIX2 but maintaining expression of the other podocyte markers, e.g., WT1+, nephrin+, podocin+, PAX2, etc. (e.g., PAX2+WT1+podocin+synaptopodin+nephrin+P-cadherin+CD2AP+ZO-1+). Phenotypically, mature podocytes have lost their ability to proliferate and demonstrate an arborized appearance with foot projections (long processes).

In an alternative embodiment, the present disclosure provides methods of differentiating mature podocyte cells, the method comprising: culturing a Brachyury+ primitive streak cell population in a nephron progenitor differentiation medium or podocyte differentiation medium free of exogenous Wnt/β-catenin activating agent, bone morphogenetic proteins (BMPs), Activin, retinoic acid (RA), vascular endothelial growth factor (VEGF) and fibroblast growth factor (FGF) for a time sufficient to differentiate a portion of the cultured cells into PAX2+WT1+podocin+synaptopodin+ nephrin+P-cadherin+CD2AP+ZO-1+ mature podocyte cells.

In some embodiments of the method of producing mature podocyte cells, at least 75% of the differentiated cells obtained in the culture are mature podocyte cells. Alternatively, at least 80% of the differentiated cells as mature podocyte cells, at least 85% of the differentiated cells as mature podocyte cells, at least 90% of the differentiated cells are mature podocyte cells, at least 95% of the differentiated cells are mature podocyte cells, at least 98% of the differentiated cells are mature podocyte cells, or at least 99% of the differentiated cells are mature podocyte cells.

In some embodiments, the time sufficient to complete steps (a)-(c) is at least 10 days, alternatively at least 12 days, alternatively at least 14 days, alternatively at least 16 days.

In another embodiment, the present disclosure provides methods of differentiating mature podocyte cells, the method comprising: i) culturing SIX2− immature podocyte cells in podocyte growth medium free of exogenous Wnt/β-catenin signaling activating agent, BMPs, Activin, RA, VEGF and FGF, for a time sufficient to differentiate into PAX2+WT1+podocin+synaptopodin+nephrin+P-cadherin+ CD2AP+ZO-1+ mature podocyte cells. Mature podocyte cells can be characterized by loss of the ability to proliferate (i.e., cell division and growth) and arborized appearance with foot projections (long processes).

The methods described above can be combined with methods of differentiating Brachyury+ primitive streak cell population from pluripotent stem cells (PSCs). In one embodiment, a Brachyury+ primitive streak cell population is obtained by differentiating pluripotent stem cells in a pluripotent stem cell differentiation medium comprising a Wnt/β-cadherin activating agent until the primitive streak cell population is obtained. The Brachyury+ primitive streak cell population can then be used in the production of nephron progenitor cells, immature podocyte cells or mature podocyte cells. In some embodiments, the differentiated cell population comprises at least 90% cells expressing brachyury. In some embodiments, at least 95% of cells in the first cell population express brachyury. In further embodiments, at least 98% of the cells express brachyury.

In some embodiments, before step (a) of the above-mentioned method, the pluripotent stem cells are cultured with the Wnt/β-catenin pathway activator for a sufficient amount of time to initiate differentiation into intermediate mesoderm through the primitive streak. In some embodiments, sufficient amount of time for step (a) is for a period of about 23 hours or more, for example about 23 hours to about 48 hours, e.g., about 23 hours, 24 hours, 25 hours, 26 hours, 27 hours, 28 hours, 32 hours, 36 hours, 40 hours, 44 hours, 48 hours, 50 hours, or other period of Wnt/β-catenin pathway signaling activation from about 23 hours to about 48 hours to obtain a first cell population characterized by the expression of one or more primitive streak markers, e.g., brachyury. In some embodiments, the cells express brachyury or one or more intermediate mesoderm markers (e.g. PAX2).

Pluripotent stem cell differentiation media and substrate conditions for culturing pluripotent stem cells, as used in the methods described herein, are well known in the art and include media that allow for the growth and passage of PSCs in culture. In some exemplary embodiments, a suitable medium for use in PSC differentiation to brachyury+ primitive streak cells includes, but is not limited to, DMEM, F12, DMEM/F12 (1:1), DMEM/F12 (1:3), DMEM/F12 (3:1), MEM, or other suitable medium.

As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity.

In some embodiments, activation of Wnt/β-catenin signaling is achieved by inhibiting Gsk3 phosphotransferase activity or Gsk3 binding interactions. While not wishing to be bound by theory, it is believed that inhibition of Gsk3 phosphorylation of β-catenin will inhibit tonic degradation of β-catenin and thereby increase β-catenin's level and activity to drive differentiation of pluripotent stem cells to an endodermal/mesodermal lineage. Gsk3 inhibition can be achieved in a variety of ways including, but not limited to, providing small molecules that inhibit Gsk3 phosphotransferase activity, RNA interference knockdown of Gsk3 (e.g., small interfering RNA), and overexpression of dominant negative form of Gsk3. Dominant negative forms of Gsk3 are known in the art as described, e.g., in Hagen, T. et al., incorporated by reference in its entirety. Expression and characterization of GSK-3 mutants and their effect on beta-catenin phosphorylation in intact cells. *J Biol Chem,* 277, 23330-5 (2002), which describes a Gsk3 having a R96A mutation.

In some embodiments, the Wnt/β-catenin signaling pathway is activated by inhibiting Gsk3 in pluripotent stem cells by contacting the pluripotent stem cells with a small molecule that inhibits Gsk3 phosophotransferase activity or Gsk3 binding interactions. Suitable small molecule Gsk3 inhibitors include, but are not limited to, CHIR99021, CHIR98014, BIO-acetoxime, BIO, LiCl, SB 216763, SB 415286, AR A014418, 1-Azakenpaullone, Bis-7-indolylmaleimide, and any combinations thereof. In some embodiments, any of CHIR99021, CHIR98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 3 μM to about 9 μM, e.g., about 3 μM, 4 μM, 5 μM, 6 μM, 7 μM, 8 μM, 9 μM or another concentration of CHIR99021 from about 3 μM to about 9 μM. In another embodiment, the small molecule Gsk3 inhibitor to be used is CHIR 98014 at a concentration ranging from about 0.1 μM to about 1 μM, e.g., about 0.1 μM, 0.2 μM, 0.3 μM, 0.4 μM, 0.5 μM, 0.6 μM, 0.7 μM, 0.8 μM, 0.9 μM or another concentration of CHIR-98014 from about 0.1 μM to about 1 μM. In another embodiment, the small molecule Gsk3 inhibitor to be used is BIO-acetoxime at a concentration ranging from about 0.1 μM to about 1 μM, e.g., about 0.1 μM, 0.2 μM, 0.3 μM, 0.4 μM, 0.5 μM, 0.6 μM, 0.7 μM, 0.8 μM, 0.9 μM or another concentration of BIO-acetoxime from about 0.1 μM to about 1 μM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK-3α/β siRNA (catalog #6301 from Cell Signaling Technology®, Danvers, Mass.), or a retroviral vector with an inducible expression cassette for Gsk3, e.g., a commercially available Tet-inducible retroviral RNAi system from Clontech (Mountain view, Calif.) Catalog No. 630926, or a cumate-inducible system from Systems Biosciences, Inc. (Mountain view, Calif.), e.g., the SparQ® system, catalog no. QM200PA-2. In other embodiments, the Wnt/β-catenin signaling pathway is activated by overexpressing β-catenin itself, e.g., human β-catenin (GenBank Accession Nos: X87838 and CAA61107.1 for nucleotide and protein sequences, respectively). In one embodiment, β-catenin overexpression is inducible β-catenin overexpression achieved using, e.g., any inducible expression systems. Alternatively, a constitutively active, stabilized isoform of β-catenin is used, which contains point mutations S33A, S37A, T41A, and S45A as described, e.g., in Baba, Y. et al. *Immunity* 23, 599-609 (2005). Constitutively active β-catenin confers multi-lineage differentiation potential on lymphoid and myeloid progenitors.

In yet other embodiments, Wnt/β-catenin signaling pathway activation in pluripotent stem cells is achieved by contacting the cells with an agent that disrupts the interaction of β-catenin with Axin, a member of the β-catenin destruction complex. Disruption of Axin-β-catenin interactions allow β-catenin to escape degradation though the destruction complex thereby increasing the net level of β-catenin to drive β-catenin signaling. For example, the Axin-β-catenin interaction can be disrupted in pluripotent cells by contacting them with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD4 Biosciences. An effective concentration of SKL2001 to activate Wnt/β-Catenin signaling ranges from about 10 μM to about 100 μM, about 20 μM, 30 μM, 40 μM, 50 μM, 60 μM, 70 μM, 80 μM, 90 μM or another concentration of SKL2001 from about 10 μM to about 100 μM.

In some embodiments, when the method begins with PSCs, step (a) occurs after the end of the Wnt/β-catenin pathway activation step, i.e., after about 2 days when the Wnt/β-catenin pathway signaling activator is removed from contact with the cultured cells. The brachyury$^+$ population is cultured in the absence of external Wnt/β-catenin pathway activators in chemically defined medium which does not contain additional exogenous factors, including, but not limited to, for example, growth factors (for example, bone morphogenetic proteins (BMPs), vascular endothelial growth factor (VEGF) or fibroblast growth factors (FGF)), Activin, and retinoic acid (RA). In one embodiment, the defined medium is free of growth factors, Activin and retinoic acid. In another embodiment, the defined medium is free of BMPS, VEGF, FGFs, Activin and RA. In suitable embodiments, the defined medium is serum free.

Typically, the cell populations obtained by the disclosed methods comprise a very high proportion of PSC-derived podocytes. Podocytes are identified by the presence of two or more podocyte markers, e.g., (PAX2, WT1, nephrin, synaptopodin, etc.). In some embodiments, the culture of the PSC-derived podocytes results in a yield of cells of about 50% to about 99% podocytes, e.g., about 52%, about 55%, about 67%, about 70%, about 72%, about 75%, about 80%, about 85%, about 90%, about 95%, about 98%, without a sorting or selecting step (e.g., FACS, MACS, etc.). The methods can be used to produce both a population of immature podocytes or mature podocytes. In some embodiments, the culture of the PSC-derived immature podocytes results in a yield of immature cells of about 50% to about 99% podocytes, e.g., about 52%, about 55%, about 67%, about 70%, about 72%, about 75%, about 80%, about 85%, about 90%, about 95%, about 98%, without a sorting or selecting step (e.g., FACS, MACS, etc.). In some embodiments, the culture of the PSC-derived mature podocytes results in a yield of mature cells of about 50% to about 99% podocytes, e.g., about 52%, about 55%, about 67%, about 70%, about 72%, about 75%, about 80%, about 85%, about 90%, about 95%, about 98%, without a sorting or selecting step (e.g., FACS, MACS, etc.). In some embodiments, the PSC-derived podocytes express two or more podocyte markers selected from the group consisting of PAX2, WT1, P-cadherin, CD2AP, podocin, synaptopodin, nephrin and ZO-1.

In some embodiments, PSC-derived immature or mature podocytes express three or more markers, four or more markers, five or more markers, six or more markers, seven or more markers, or all eight of the markers selected from the group consisting of PAX2, WT1, P-cadherin, CD2AP, podocin, synaptopodin, nephrin and ZO-1.

In some embodiments, at least 75% of PSC-derived immature podocyte cells produced by the methods described above express two or more of the podocyte markers selected from the group consisting of PAX2, WT1, P-cadherin, CD2AP, podocin, synaptopodin, nephrin and ZO-1, alternatively at least 80%, alternatively at least 85%, alternatively at least 90%, alternatively at least 95%, alternatively at least 98%, alternatively at least 99% of the PSC-derived podocyte progenitor populations produced by the methods described above express two or more of the podocyte markers selected from the group consisting of PAX2, WT1, P-cadherin, CD2AP, podocin, synaptopodin, nephrin and ZO-1. In some embodiments, at least about 75%, alternatively about 80%, alternatively about 85%, alternatively about 90%, alternatively at least 95%, alternatively at least 98%, alternatively at least 99% of the PSC-derived immature podocytes produced by the methods described above express the podocyte markers PAX2, WT1, and nephrin. In some embodiments, at least about 75%, alternatively about 80%, alternatively about 85%, alternatively about 90%, alternatively at least 95%, alternatively at least 98%, alternatively at least 99% of the PSC-derived nephron progenitors produced by the methods described above express the podocyte markers PAX2, WT1, nephrin and synaptopodin. In another embodiment, at least about 75%, alternatively about 80%, alternatively about 85%, alternatively about 90%, alternatively at least 95%, alternatively at least 98%, alternatively at least 99% of the PSC-derived mature podocyte produced by the methods described above express the podocyte markers PAX2, WT1, P-cadherin, CD2AP, podocin, synaptopodin, nephrin and ZO-1.

Suitable time for step (a)-(c) to produce PSC-derived immature podocytes includes at least 10 days, alternatively at least 16 days, alternatively at least 20 days, and includes periods of time greater than 10 days, for example, 11 days, 12, days, 13 days, 14 days, 16 days, 17 days, 18 days, 19 days, 20 days, 21 days, etc.

The PSC-derived immature podocytes of the present methods can be further differentiated into mature, non-differentiating podocytes by subsequent incubation at a differentiation-permissive temperature, for example, 37° C. Mature podocytes can be characterized by losing expression of SIX2 but maintaining expression of the other podocyte markers, e.g., WT1$^+$, nephrin$^+$, podocin$^+$, PAX2, etc. Phenotypically, mature podocytes have lost their ability to proliferate and demonstrate an arborized appearance with foot projections.

As disclosed herein, in some embodiments of the methods for differentiating nephron progenitors or podocytes from PSCs, the culturing steps can be conducted without including exogenous growth factors and the cultures can be completely chemically-defined. Specifically, both culturing conditions of step (a), (b) and (c) can be chemically-defined and the culture conditions are free of one or more exogenous factors for example, growth factors, including, but not limited to, bone morphogenetic proteins (BMPs), vascular endothelial growth factor (VEGF), or fibroblast growth factor (FGF). Additionally the culture conditions may be free of additional exogenous factors, including Activin and retinoic acid (RA), In some embodiments of this and other aspects described herein, the pluripotent stem cells and/or differentiating cells can be cultured as adherent cells during the culturing steps. While not necessary, it can be desirable to provide a cell culture environment that mimics the environment of the kidney. In some embodiments, the cells can be cultured on a solid substrate surface coated with at least one extracellular matrix wherein the cells in culture are associated with the matrix. Examples of suitable extracellular matrices, include, but are not limited to, laminin, collagen, fibronectin, vitronectin, hyaluronic acid, peptides, gelatin, Matrigel®, decellularized matrix, and a combination of one or more of the above. In some embodiments, the surface may be coated with decellularized matrix produced by glomerular endothelial cells. Other suitable substrates on which to culture the cells include, but are not limited to, Matrigel®substrate (BD Bioscience, NJ), Synthemax® surfaces (Corning), and vitronectin-coated surfaces.

Suitable substrate surfaces can also be provided as part of any cell- or tissue culture device, including, but not limited to, transwell, a microwell, a microfluidic device, a bioreactor, a culture plate or any combination thereof. In some embodiments, the podocytes can be included in a 3D printing system to generate artificial kidney tissue. In another embodiment, the microfluidic device may be an organ-on-a-chip device.

In some embodiments, the cells may be grown in association with an engineered 3D substrate or on a chip to reconstitute kidney glomerular/capillary-wall function for in vitro studies. Conventional tissue culture conditions fail to reproduce the structural and functional characteristics of the glomerulus. Therefore, suitable 3D substrates including 3D printed substrates, porous membranes, and chips may be used in combination with other cell types, e.g., endothelial cells, to recapitulate the cell-cell interactions within the glomerulus. In one embodiment, the substrate may be a synthetic tissue scaffold that may, in some instances, comprise a biopolymer. Suitable embodiments may provide a synthetic tissue scaffold and a population of PSC-derived podocytes distributed therein, wherein the PSC-podocytes are made by the methods described herein. In some embodiments, the synthetic tissue scaffold may include one or more kidney-associated cells distributed in the biopolymer in addition to the podocytes. Suitable kidney-associated cells include, but are not limited to, for example, endothelial cells, mesangial cells, epithelial cells, smooth muscle cells or myocytes, granular cells, parietal cells, loop of Henle thin segment cells, proximal tubular cells, duct cells, connective tissue fibroblasts, pericytes, and a combination of two or more thereof.

The PSC-derived podocytes produced by the methods herein can be used for various applications including, for example, but not limited to, in vitro models for kidney/glomerular disorders, therapeutic applications, e.g., tissue regeneration and/or repair or transplantation, drug discovery and/or development, and tissue engineering.

Therapeutic use of the cultured podocytes described herein include any diseases in which podocytes dysfunction, for example, the treatment of chronic kidney diseases, glomerular disease and end-stage renal diseases.

Chronic kidney disease (CKD), also called chronic kidney failure, is characterized by the gradual loss of kidney function. When chronic kidney disease reaches an advanced stage, dangerous levels of fluid, electrolytes and wastes can build up in your body. Treatment for chronic kidney disease focuses on slowing the progression of the kidney damage, usually by controlling the underlying cause. Chronic kidney disease can progress to end-stage kidney failure, often called end-stage renal disease (ESRD) which is fatal without artificial filtering (dialysis) or a kidney transplant. One of the major causes of CKD is glomerular diseases.

Glomerular diseases include many conditions with a variety of genetic and environmental causes, but they fall into two major categories, glomerulonephritis (the inflammation of the membrane tissue in the kidney that serves as a filter, separating wastes and extra fluid from the blood), and glomerulosclerosis (scarring or hardening of the tiny blood vessels within the kidney). Many glomerular diseases are due to a spectrum of podocytopathies (disorders of the podocyte). Diabetes and hypertension are leading causes of CKD and have associated podocyte injury and depletion.

Since podocyte injury is common to all glomerular diseases and podocyte depletion is associated with rapidly progressive kidney disease and the development of ESRD, many of these diseases may be treated by administration of podocytes differentiated by these methods. Suitable kidney diseases that may be able to be treated using the in vitro differentiated podocytes include, but are not limited to, chronic kidney disease, including, but not limited to, for example, congenital nephrotic syndrome, diffuse mesangial sclerosis, and Alport syndrome, and glomerular diseases. ESRD may also be treated using the podocytes differentiated by the methods described herein.

In some embodiments, the present disclosure provides methods of treating a subject having disease associated with dysfunctional podocytes, the method comprising administering to the subject an effective amount of podocytes produced by the methods described herein to treat the subject having the disease. In one embodiment, the disease is CKD or a glomerular disease. In another embodiment, the disease is end stage renal disease.

The term "treating" or "treatment" includes, but is not limited to, reducing, inhibiting or preventing one or more signs or symptoms associated with the disease or disorder. For example, treating CKD or a glomerular disease include, for example, but are not limited to, providing functional podocytes and improving one or more symptom associated with CKD or glomerular disease (e.g., restoring partial kidney function).

Pluripotent stem cells (PSCs) suitable for the differentiation methods described herein include, but are not limited to, hESCs, human induced pluripotent stem cells (hiPSCs) non-human primate embryonic stem cells (nhpESCs), non-human primate induced pluripotent stem cells (nhpiPSCs). The examples below show the ability to produce human podocytes from both human hESCs and hiPSCs. In a preferred embodiment, the methods use hPSCs, including both hESCs and hiPSCs.

In some embodiments, at least 70% or higher, including, e.g., at least about 80% or more, at least about 90% or more, at least about 95% or more (up to 100%) of the pluripotent stem cells can be differentiated into podocytes.

Podocytes of the present invention can be cryopreserved at any time during the culture process, and the differentiation can be resumed after the cells are thawed. Cryopreservation media are known in the art. Further, immature podocytes made by the described method may be cryopreserved, and later thawed to proliferate and expand in culture when required.

In some embodiments, kits for carrying out the methods of the present disclosure are provided. For example, a kit for culturing podocytes from pluripotent stem cells is provided. Such kits may include (a) a pluripotent stem cell differentiation medium, and (b) a nephron progenitor medium. In some embodiments, the kit may include (a) a pluripotent stem cell differentiation medium and a Wnt/β-catenin activator, for example a Gsk3 inhibitor, and (b) a nephron progenitor medium. The kit may further comprise (c) a podocyte differentiation medium and optionally B-27®. In another embodiment, the kit may include (a) a nephron progenitor medium and (b) a podocyte differentiation medium and optionally B-27®.

Additionally, instructions on how to culture cells are provided. In some embodiments, pluripotent stem cells that can be used for the methods are also provided in the kit. Further in some embodiments, the kits may further comprise a solid substrate on which to grow the cells, the substrate may or may not be coated with a suitable material to promote cell adhesion, e.g., extracellular matrix proteins.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Differentiation of hPSC-Derived Podocytes

This example demonstrates a facile method to differentiate hPSCs into podocytes by small molecule activation of Wnt signaling and subsequent culture in podocyte-permissive media. In this method, hPSCs are first differentiated into primitive-streak mesoderm and intermediate mesoderm, then the differentiated cells progress to podocyte progenitors and immature podocytes and finally into mature podocytes that express key podocyte-related proteins, including PAX2, WT1, nephrin and synaptopodin. These hPSC-derived podocytes also exhibit podocyte phenotypes, including albumin uptake, and cell death upon TGF-β1 stimulation. This differentiation method has the potential to generate quantities of podocytes for disease modeling, drug screening, and development of podocyte cell therapies.

Wnt Activation Directs hPSCs to Primitive Streak and Intermediate Mesoderm

Most cells forming the kidney, including podocytes, originate from intermediate mesoderm[31]. Wnt signaling plays an important role in the development of mesodermal lineages and induction of canonical Wnt signaling has been used to direct hPSC differentiation into mesoderm[32-34]. For example, a prior study showed that treatment of undifferentiated hPSCs with 6 µM CHIR99201, a GSK3β inhibitor, in a serum-free and albumin-free medium generated a uniform population of cells expressing primitive streak markers after 24 hours[35]. Thus, as a first step toward differentiating hPSCs into podocytes, induced hPSCs (iPSCs) were seeded on a Matrigel®-coated surface at a density of ~2×10$^4$ cells/cm$^2$ in mTeSR®1. After 3 days of expansion to a density of 6×10$^4$ cells/cm$^2$, the hPSCs were treated with 6 µM CHIR99201 for 48 hr in serum-free and albumin-free podocyte medium 1 (PM1: DMEM/F12, 1% MEM-NEAA, 0.5% GlutaMAX, 0.1 mM β-mercaptoethanol) (FIG. 1A). Before initiating differentiation at day 0, expression of pluripotent markers OCT4, NANOG and TRA-1-60 was validated by immunofluorescence (FIG. 1B-D). After 24 hr treatment with CHIR99201, the cells uniformly expressed the primitive streak marker brachyury, which localized to the nucleus with nearly 100% positive population (FIG. 1E, 1F). As expected, brachyury expression was transient, disappearing after day 3 (FIG. 1G). After 48 hr CHIR99201 treatment in PM1, the medium was switched to serum-free podocyte medium 2 (PM2: human endothelial serum-free medium (hESFM), 2% B-27®) and cultured to day 16. The kinetics of primitive streak induction were assessed by immunofluorescence and qRT-PCR. The primitive streak gene MIXL1 reached peak expression at 24 hour and then was undetectable after day 4 (FIG. 1H, I). At day 4, nearly 100% of the cells expressed the intermediate mesoderm marker PAX2, which localized to the nucleus (FIG. 1J). Expression of the pluripotency gene POU5F1 dramatically decreased after initiation of differentiation (FIG. 1K).

Primitive Streak Cells Progress to Podocyte Progenitors

Figures 2A, 2B, 2C, 2D:
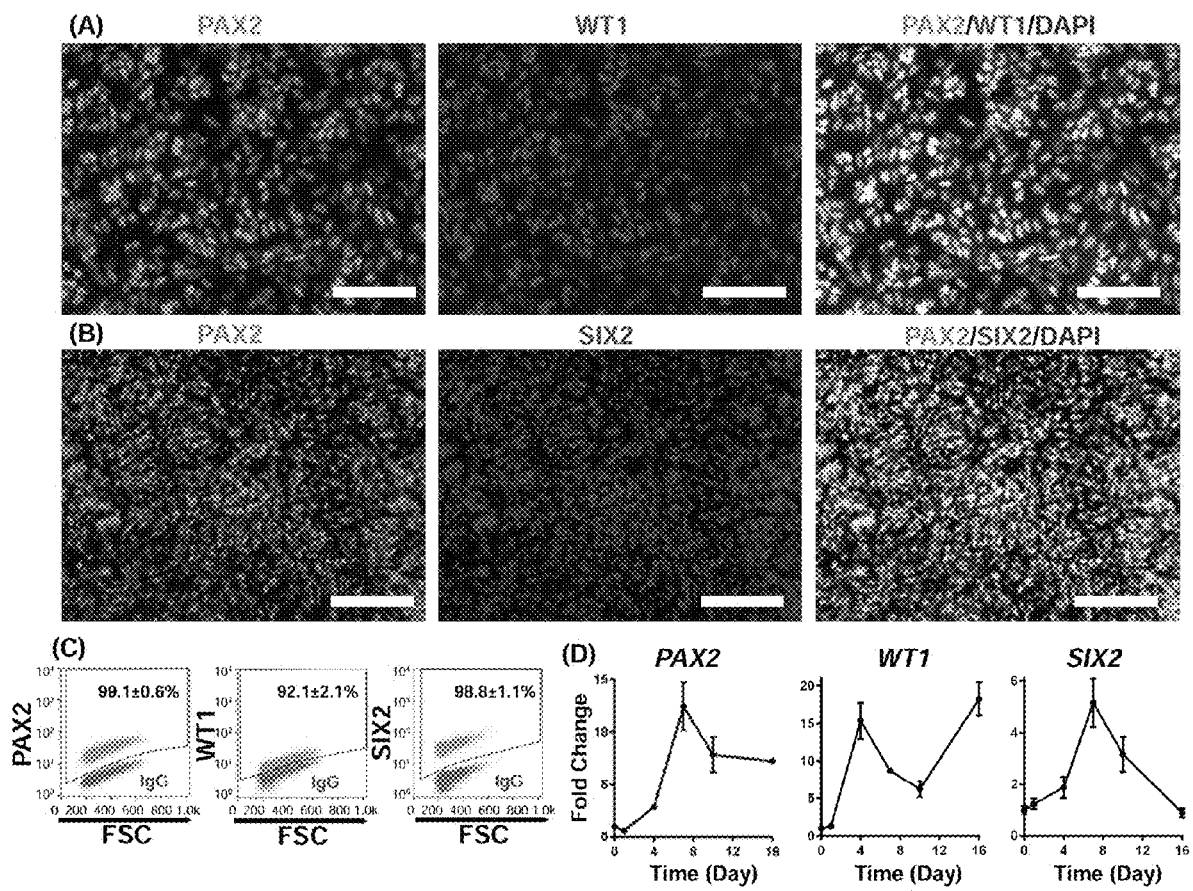
FIGS. 2A-2D. Using the methods described in FIG. 1, cells progress from primitive streak to nephron progenitors at day 6. At differentiation day 6, cells were assessed by immunofluorescence and flow cytometry for podocyte progenitor markers, including PAX2 and WT1 (A, C), and SIX2 (B, C). In (C), red dots represent isotype control treated cells used to identify the gated regions and blue dots represent cells stained for the indicated marker. Numbers indicate the fraction of stained cells (blue) in the gated regions. (D) Quantitative RT-PCR was used to measure the expression of PAX2, WT1, SIX2 relative to housekeeping gene GAPDH during IMR90-4 iPSC differentiation to podocytes using the protocol illustrated in FIG. 1A. Expression levels were normalized to undifferentiated IMR90-4 iPSCs. Data are represented as mean±SEM of three replicates. Scale bar, 100 μm.

At day 6, immunofluorescence analysis indicated that the differentiating cells possessed nuclear localization of nephron progenitor proteins PAX2, WT1 and SIX2 (FIG. 2A, B). Both PAX2 and WT1 are expressed in nephron progenitors and mature podocytes, while SIX2 is transiently expressed in nephron progenitors[36]. At day 6 over 90% of the cells expressed PAX2, WT1 and SIX2, as determined by flow cytometry (FIG. 2C). By qRT-PCR, PAX2 and WT1 expression gradually increased through day 5 and remained expressed through day 16 of differentiation. SIX2 expression peaked at day 7 and then decreased afterwards (FIG. 2D).

Figures 3A, 3B, 3C, 3D, 3E, 3F, 3G, 3H, 3I:
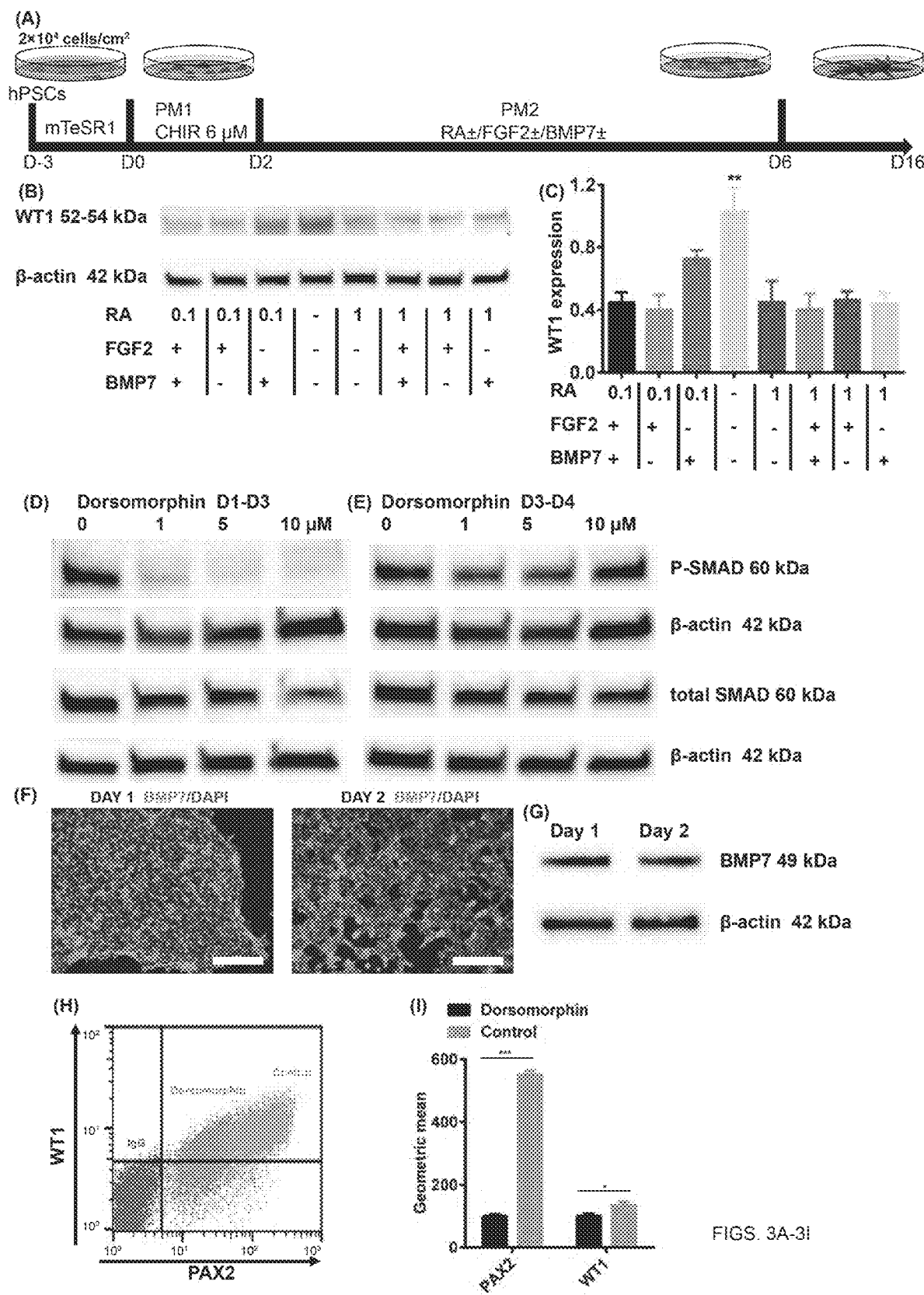

Although we observed cells expressing podocyte markers in the growth factor-free PM2 medium, BMP4 and BMP7[37-39], retinoic acid (RA)[40, 41] and FGF2[42] have previously been shown to be involved in kidney development. Thus we examined whether addition of these factors would alter the conversion of iPSCs to nephron progenitors. After 2 days of canonical Wnt pathway activation by CHIR99021, cells were treated with different combinations of BMP7, RA, and FGF2 from day 2 to day 6 (FIG. 3A) in PM2 after which we assessed whether these factors enhanced specification of primitive streak cells to WT1$^+$ nephron progenitors by Western blot. The Western blot data show that cells differentiate from primitive streak cells by progressing into WT1+ podocyte precursors at day 6. Unexpectedly, the results showed the greatest WT1 expression in the absence of exogenous BMP7, RA, or FGF2 (FIG. 3B, C). Highest WT1 expression level with added factors was about 70% of WT1 in the absence of exogenous BMP7, RA and FGF2 (FIG. 3B, C), so subsequent experiments were performed in the absence of these 3 factors.

Since WT1 expression was observed in the absence of exogenous BMPs, Wnt activation-induced endogenous BMP signaling was investigated. In the absence of dorsomorphin, which inhibits BMP type I receptors and blocks BMP-induced SMAD1/5/8 phosphorylation, the CHIR99021-treated cells exhibited high levels of phosphorylated SMAD1/5/8 (P-SMAD) at day 3 (FIG. 3D). However, when dorsomorphin was added from days 1-3 of differentiation, SMAD phosphorylation was completely inhibited at dorsomorphin concentrations higher than 5 µM. When dorsomorphin was added after removal of CHIR99021 (from day 3 to day 4), SMAD phosphorylation at day 4 was unaffected (FIG. 3E). Endogenous BMP7 was confirmed by immunofluorescence and Western blot with cells at differentiation day 1 and day 2 (FIG. 3F, G).

We then tested if dorsomorpin treatment inhibited nephron progenitor differentiation to assess whether endogenous BMP production plays a role in podocyte specification. Cells were analyzed for PAX2 and WT1 expression by flow cytometry at day 16 of differentiation. Cells treated with 1 µM dorsomorphin from day 1 to day 3 differentiated to WT1 and PAX2-expressing cells, although the expression level was significantly lower than the untreated control (FIG. 3H, I). Together these results suggest that while Wnt activation is sufficient to differentiate hPSCs into podocytes progenitors, endogenous BMP7 signaling may also play a role.

Nephron Progenitors Become Mature Podocytes

Figures 4A, 4B, 4C, 4D, 4E:
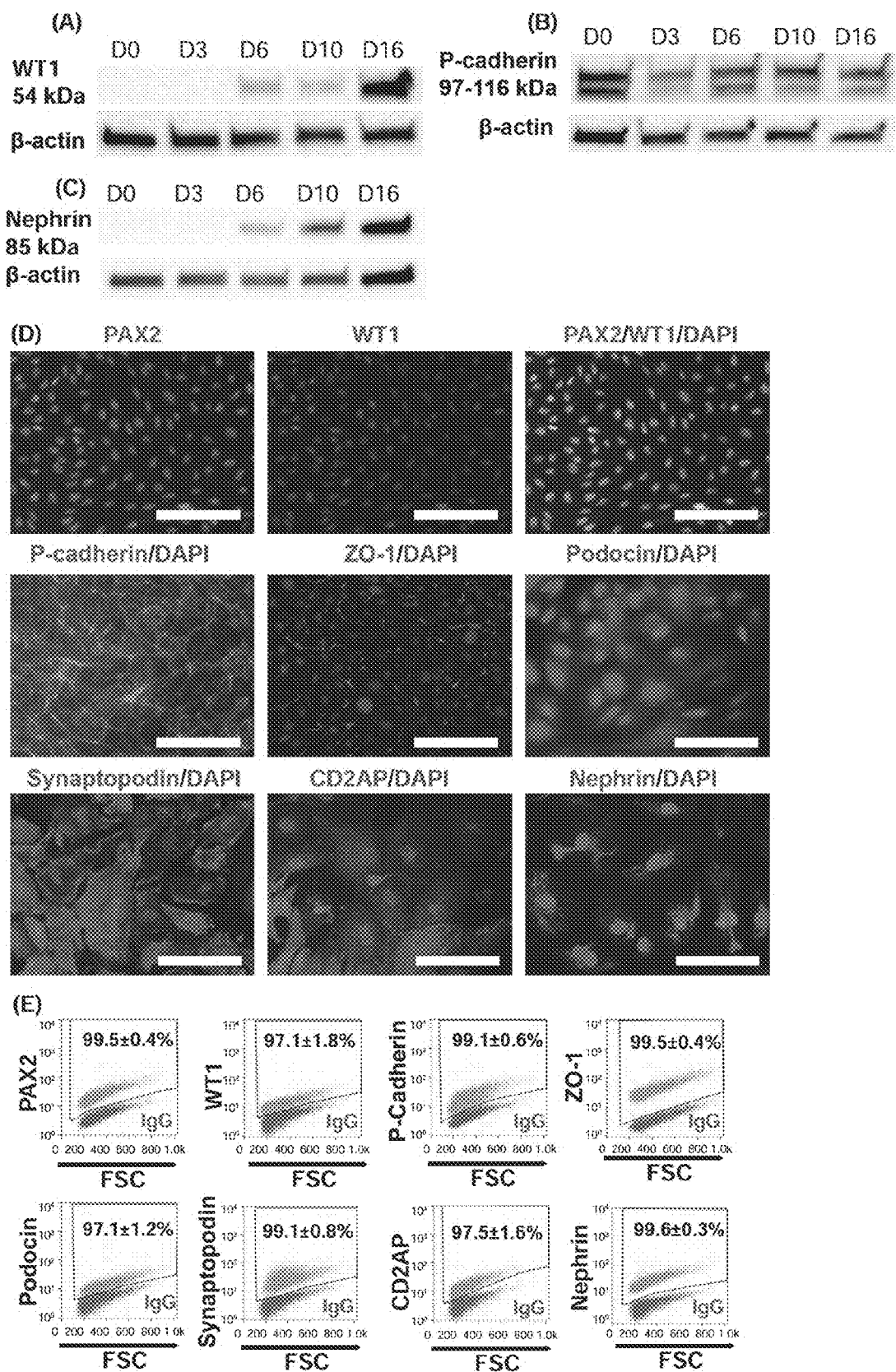
FIGS. 4A-4E. hPSC-derived podocyte cells express key podocyte markers. (A) hPSCs were differentiated as illustrated in FIG. 1A. Cell lysates were collected at day 0, day 3, day 6, day 10, day 16 of differentiation. Western blot was used to assess the expression of WT1 (A), P-cadherin (B), synaptopodin (C) and nephrin (C). At day 16, cells differentiated as shown in FIG. 1A were characterized by immunofluorescence (D) and flow cytometry (E) for expression of the indicated podocyte proteins. Scale bar, 100 μm. In (E), red dots represent isotype control treated cells used to identify the gated regions and blue dots represent cells stained for the indicated marker. Numbers indicate the fraction of stained cells (blue) in the gated regions. Data are presented as mean±SEM of three independent experiments. See also FIGS. 7-11.
Figure 7:
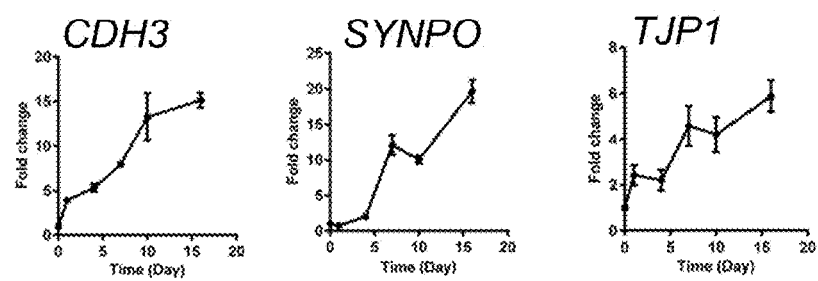
FIG. 7. Gene expression during podocyte differentiation. Quantitative RT-PCR was used to quantify the expression of the podocyte markers CDH3 (P-cadherin), SYNPO and TJP1 during hPSC differentiation to podocytes using the process illustrated in FIG. 1A. GAPDH was used as an endogenous housekeeping gene control and expression level was normalized to day 0. Data are presented as mean±SEM of three biological replicates.

Nephron progenitors differentiated as shown in FIG. 1A were characterized for acquisition of podocyte markers throughout the differentiation process by both qRT-PCR and Western blot. CDH3 (P-cadherin), SYNO (synaptopodin) and TJP1 (ZO-1) expression gradually increased during the 16 day differentiation process (FIG. 7). WT1 protein was first detected at day 6 and was significantly more abundant at day 16 (FIG. 4A). P-cadherin is a cell-cell adhesion molecule that maintains the integrity of epithelial tissues[44] and is expressed in hPSCs[45]. P-cadherin expression slightly decreased after iPSCs progressed to primitive streak and intermediate mesoderm at day 3 of differentiation (FIG. 4B). P-cadherin expression then increased and remained relatively constant from days 6-16. Both synaptopodin and nephrin are involved in the formation of the slit diaphragm[46, 47]. During the differentiation process, synaptopodin was expressed at day 10 and afterwards, while significant nephrin expression was detected at day 6 and expression increased through day 16 (FIG. 4C). Immunofluorescence images were acquired at day 16 to show the localization of the key podocyte proteins (FIG. 4D).

Figures 8A, 8B:
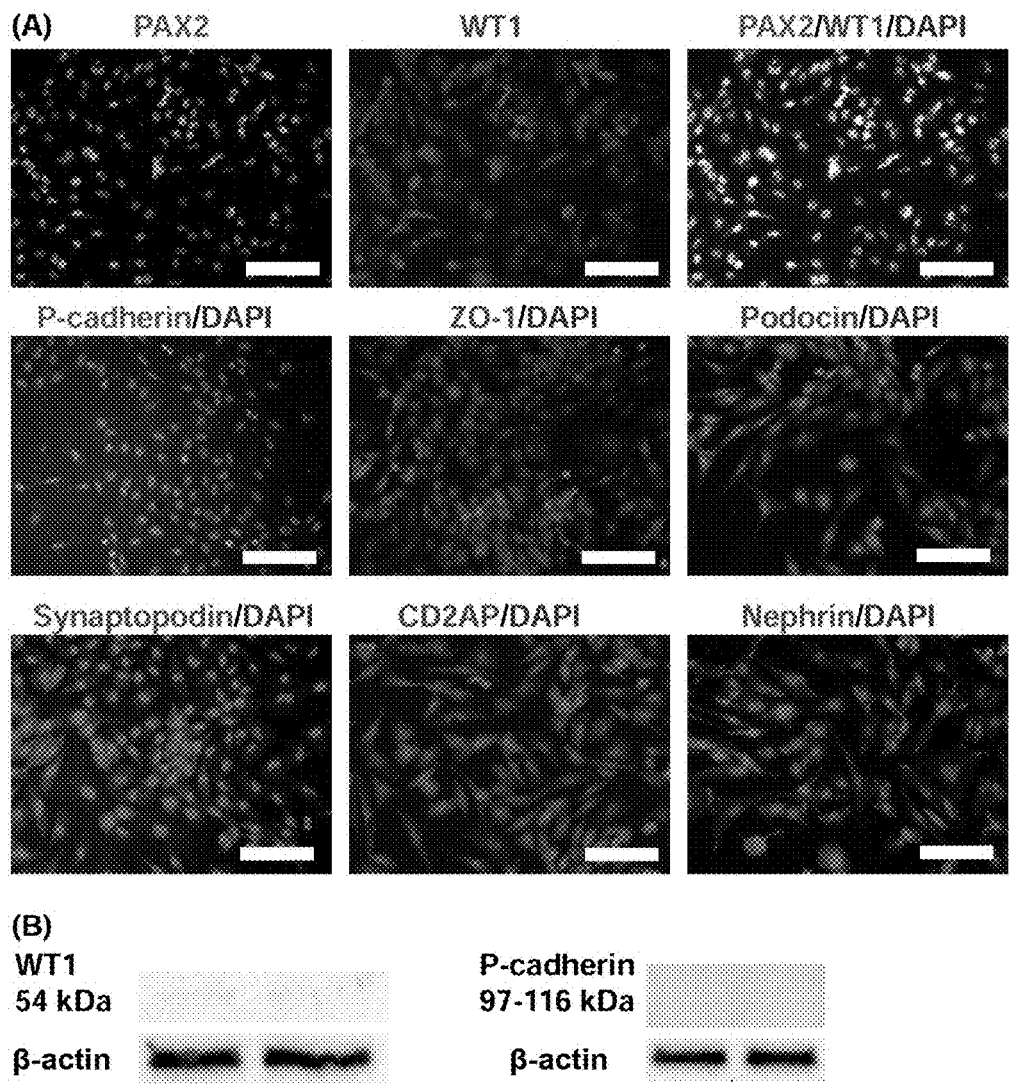
FIGS. 8A-8B. Expression of podocyte markers on human primary podocytes. (A) Most major podocyte proteins, including PAX2, WT1, podocin, synaptopodin, ZO-1, CD2AP and nephrin were also expressed by primary podocytes. In the primary podocytes, the WT1 was not exclusively localized to the nucleus while P-cadherin expression was not detected. (B). Significant expression of WT1 or P-cadherin was not found in primary podocytes as assayed by western blot.
Figures 9A, 9B, 9C, 9D:
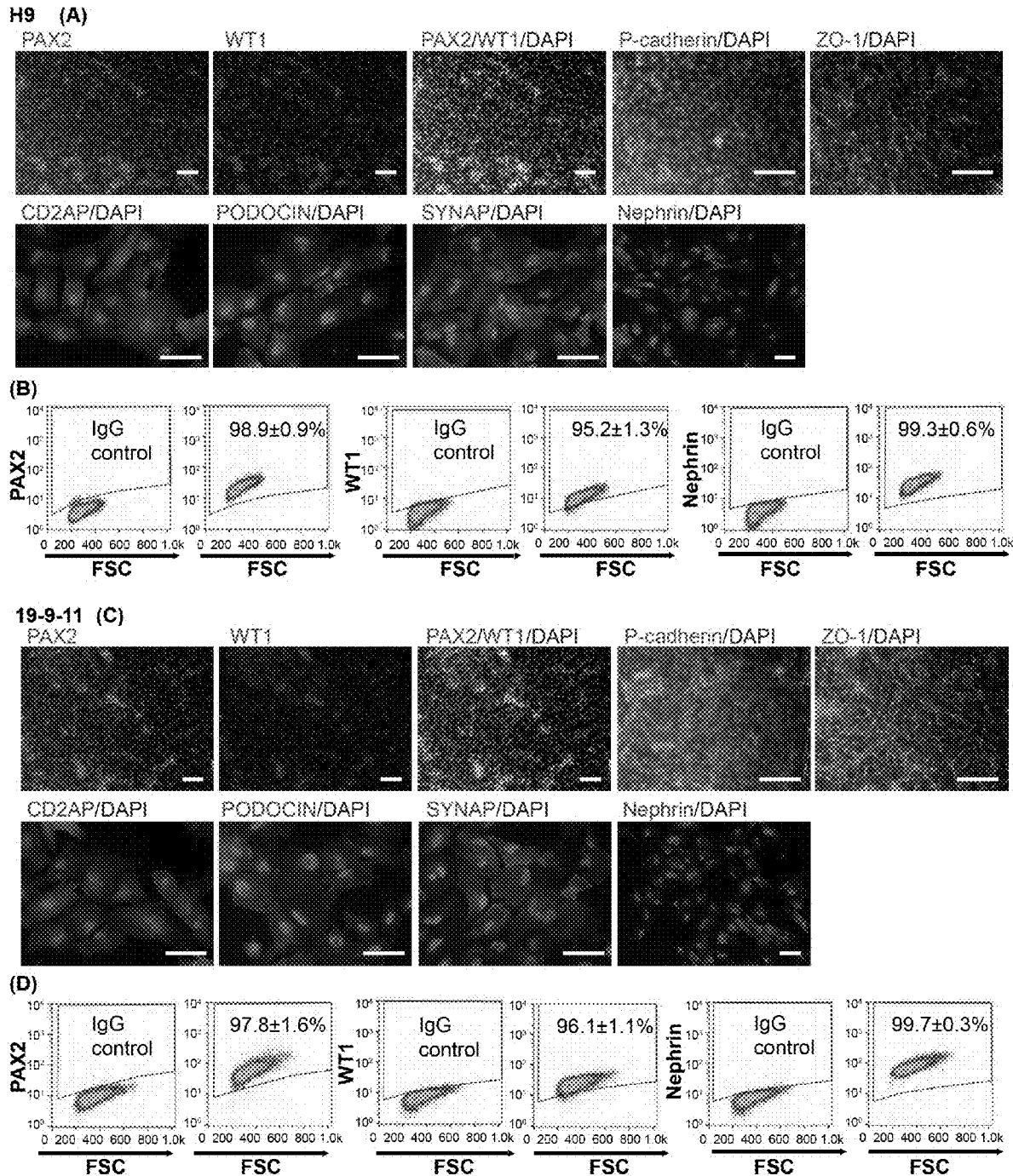
FIGS. 9A-9D. Podocytes differentiated from H9 hESCs and 19-9-11 iPSCs express podocyte-related proteins. H9 A(10A and 10B), a line of human embryonic stem cells and 19-9-11 (10C and 10D), a line of human induced pluripotent stem cells, were used to differentiate podocytes. Podocytes were differentiated as illustrated in FIG. 1A. At day 16, cells were characterized by immunofluorescence (10A, 10C) and flow cytometry (10B, 10D) for the indicated markers. Scale bar, 100 μm. Cells for H9-podocytes were from day 34.
Figures 10A, 10B, 10C, 10D:
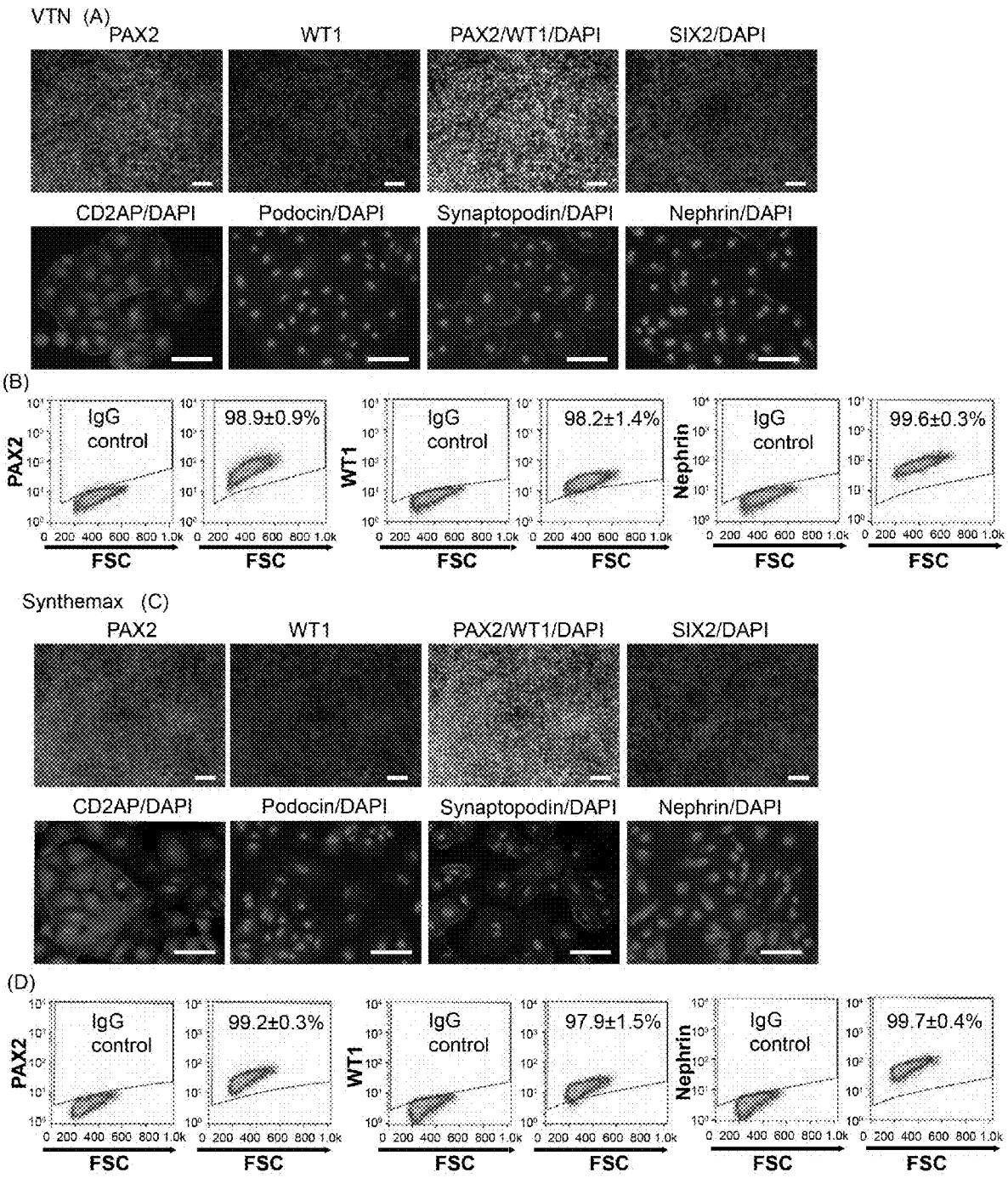
FIGS. 10A-10D. Podocytes differentiated on surfaces coated with Synthemax® or vitronectin express podocyte-related proteins. Podocytes were differentiated as illustrated in FIG. 1A on surfaces coated with either Synthemax® (9C and 9D) or vitronectin (9A and 9B). At day 16, cells were characterized by immunofluorescence (9A and 9C) and flow cytometry (9B and (D) for the indicated markers. Scale bar, 100 μm.

Nearly 100% of the day 16 IMR90-4 iPSC-derived podocytes expressed key podocyte proteins, including PAX2, WT1, P-cadherin, podocin, synaptopodin, CD2AP, nephrin and ZO-1, demonstrating the production of virtually pure podocytes from iPSCs (FIG. 4E). We also compared the expression of key podocyte proteins between hPSC-derived podocytes and human primary podocytes. Most major podocyte proteins, including PAX2, WT1, podocin, synaptopodin, ZO-1, CD2AP and nephrin were also expressed by primary podocytes. However, in the primary podocytes, the WT1 was not exclusively localized to the nucleus while P-cadherin expression was not detected, nor did we detect significant expression of WT1 or P-cadherin in primary podocytes by western blot (FIG. 8A-8B).

We then tested the differentiation protocol illustrated in FIG. 1A in two additional hPSC lines. At day 16, nearly 100% of the cells differentiated from both H9 hESCs and 19-9-11 iPSCs expressed key podocyte proteins, including PAX2, WT1, P-cadherin, ZO-1, CD2AP, podocin, synaptopodin, and nephrin (FIG. 9A-D). To further define the differentiation system, we also tested podocyte differentiation on defined substrates, Synthemax® and vitronectin, as replacements for Matrigel®. Almost 100% of the cells differentiated on both Synthemax®- and vitronectin-coated surfaces showed high expression of podocyte proteins, similar to differentiation on Matrigel® (FIG. 10A-D). For IMR90-4 iPSC line, we performed the optimized differentiation process more than 30 times. For both H9 ESCs and 19-9-11 iPSCs, we performed the experiments at least three independent times. For differentiation on Synthemax- and vitronectin-coated surfaces, we performed experiments at least three times.

hPSC-Derived Podocytes Exhibit Key Podocyte Phenotypes

Given the marker expression profile characteristic of podocytes, we examined several podocyte phenotypes at day 16. Nephron progenitors are proliferative and exhibit a cobblestone-like morphology in primary cell culture[48]. IMR90-4 iPSC-derived nephron podocytes exhibited a cobblestone-like shape at day 6 of differentiation (FIG. 5A), very similar to the morphology of primary human podocytes under standard culture conditions (FIG. 11A). After 16 days, these iPSC-derived podocyte cells formed a monolayer of large arborized cells exhibiting prominent thin processes (FIG. 5 B,C), consistent with the morphology of cultured immortalized fully differentiated podocytes[18]. The primary cells obtained did not exhibit widespread cell body and thin process.

Figures 5A, 5B, 5C, 5D, 5E:
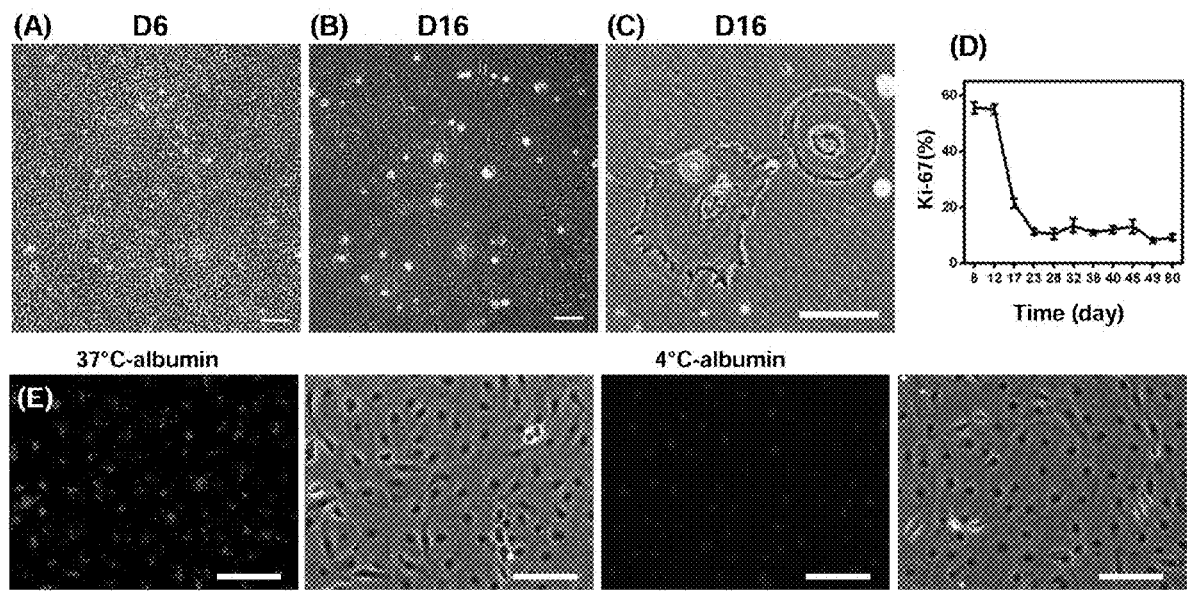
FIGS. 5A-5E. hPSC-derived podocytes exhibit key podocyte phenotypes. IMR90-4 iPSC-derived podocytes were differentiated as illustrated in FIG. 1A. Phase contrast images of IMR90-4 iPSC-derived podocytes were taken at (A) day 6, and (B-C) day 16. (D) Proliferation of cells at different time points was assessed by flow cytometry for Ki67. (E) IMR90-4 iPSC-derived podocytes at day 16 were analyzed with an Albumin Uptake Assay Kit. Alexa Fluor™ 555-labelled albumin is shown in red on a merged DAPI image and the corresponding bright field image is provided on the right. 4° C. was used as a control to prevent endocytosis. Scale bars, 100 μm.

Similarly, IMR90-4 iPSC-derived podocytes lost proliferative capacity during differentiation, as determined by Ki-67 staining, after day 12 of the differentiation. By day 22 only about 10% of cells expressed Ki-67 (FIG. 5D). At day 16, 70±10 podocytes were produced per undifferentiated iPSC at day 0, indicating substantial expansion during the differentiation process. Thus, by day 16 of differentiation, the iPSCs have progressed through a nephron progenitor stage to non-proliferative cells expressing hallmark podocyte markers.

Figures 6A, 6B, 6C:
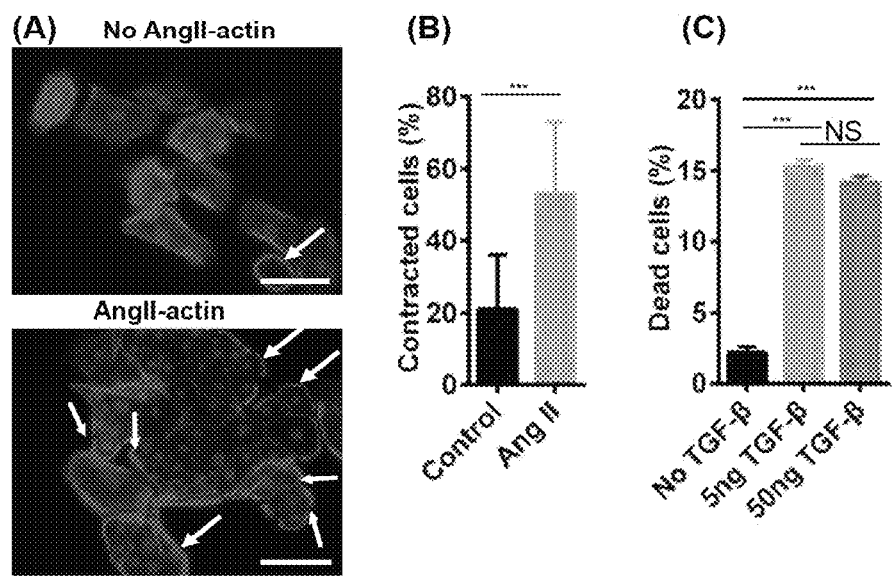
FIGS. 6A-6C. hPSC-derived podocyte cells exhibit actin reorganization after angiotensin II treatment and cell death is induced by TGF-β1 treatment. hPSC-derived podocytes were differentiated as illustrated in FIG. 1A. At day 16, cells were treated with 500 ng/mL Ang II for 6 hr and phalloidin staining was used to assess changes in cytoskeletal structure. White arrows indicate the cells with peripheral F-actin. (B) More than 200 cells over 15 images were analyzed and the percentage of cells with peripherally-organized actin was calculated for control and Ang II-treated cells. Data are presented as mean percentage±SEM of three independent experiments over 15 images. Scale bars, 100 μm. (C) At day 16, cells were treated with 5 ng/mL and 50 ng/mL TGF-β1 for 24 hr. Detached cells were collected from the medium and combined with Accutase®-dissociated cells from the substrate. Cells were treated with trypan blue and the numbers of cells incorporating and excluding trypan blue were counted on a hemocytometer. Percentage of dead cells was calculated as the number of cells that incorporated trypan blue divided by the total cell number. Data are presented as mean±SEM of three independent experiments.

Podocytes uptake albumin via endocytosis and degrade albumin in lysosomes[52,53]. We assessed the ability of day 16 iPSC-derived podocytes to endocytose Alexa Fluor 555-labeled albumin in a temperature-dependent manner. At 37° C., the iPSC-derived podocytes contained extensive fluorescence in intercellular vesicles, while the cells at 4° C., where endocytosis is inhibited, did not incorporate albumin (FIG. 5E). We further confirmed temperature-dependent albumin uptake in human primary podocytes (FIG. 11B). Next, angiotensin II (Ang II) induces podocyte damage and glomerular disease in part by altering cytoskeletal structure and inducing contractility[54]. To examine the effects of Ang II, we treated day 16 iPSC-derived podocytes with 500 ng/mL Ang II for 6 hr. Ang II-treated cells displayed a reorganized actin morphology compared to untreated cells (FIG. 6A, indicated with white arrows). Over 50%, of the IMR90-4 iPSC-derived podocytes exhibited peripheral actin upon Ang II stimulation, while only about 20% of control cells exhibited peripheral actin (FIG. 6B). Finally, TGF-β1 induces cell death in primary and immortalized podocytes[55,56]. Hence, we tested the effects of TGF-β1 treatment on day 16 IMR90-4 iPSC-derived podocyte viability. iPSC-derived podocytes exposed to 5 or 50 ng/mL TGF-β1 for 24 hr exhibited a significantly higher percentage of dead cells than the control (15% vs. 2%) as assessed by trypan blue uptake (FIG. 6C). Taken together, iPSC-derived podocytes display phenotypes that have been described for terminally differentiated podocytes.

Discussion

In this Example, we demonstrate a simple method to differentiate hPSCs into terminally-differentiated podocytes in a defined system. After treatment with the small molecule GSK3 inhibitor CHIR99021, hPSCs differentiate in a developmentally-relevant progression from the pluripotent stage through primitive streak-like cells, nephron progenitors and eventually to mature podocytes that express key podocyte proteins, including PAX2, WT1, podocin, synaptopodin and nephrin. Fully differentiated podocytes do not proliferate significantly in vivo or in vitro[57]. Likewise, hPSC-derived podocytes lost proliferative capacity after day 16 of differentiation. Importantly, hPSC-derived podocytes exhibit key podocyte phenotypes, including actin reorganization upon Ang II stimulation, albumin uptake and induction of cell death upon TGF-β1 treatment. This differentiation protocol employs a defined system, including serum-free culture medium as well as a defined extracellular matrix. Defined systems generally enhance reproducibility and facilitate production of cells for therapeutic applications[58, 59].

In vivo, the majority of cell types forming the kidney, including podocytes, originate from intermediate mesoderm[34]. Canonical WNT signaling activation has been shown to play an important role in the differentiation of hPSCs into intermediate mesoderm[35-37]. Previously, several studies have shown that Wnt pathway activation combined with BMP4, BMP7, RA and FGF2 treatment is essential to differentiate hPSCs into podocytes[32,33,42]. We determined that application of 6 μM CHIR99021 alone, in a podocyte permissive medium, was sufficient to direct three different hPSC lines into intermediate mesoderm that then became nephron progenitors and eventually virtually pure populations of mature podocytes as assessed by flow cytometry for podocyte markers. We also found that BMP7, RA or FGF2 treatment actually diminished WT1 expression in the hPSC-derived podocytes. Moreover, in the differentiation process described here, BMP7 was endogenously expressed and SMAD1/5/8 activated in the differentiating hPSCs. Treatment with the BMP inhibitor dorsomorphin dramatically decreased podocyte differentiation efficiency, suggesting this endogenous BMP signaling is necessary for podocyte specification. This finding is consistent with a prior report that canonical Wnt signaling activates the BMP pathway in skeletal myoblasts by inducing BMP4 expression[60]. While it is not clear why BMP7 addition reduced WT1 expression, autocrine or paracrine BMP signaling appears to be necessary for podocyte specification in our differentiation process, perhaps induced as a consequence of Wnt pathway activation[61], obviating the need for exogenous BMP ligands, as required by all other reported podocyte differentiation protocols. Compared to previous podocyte differentiation protocols[32,33,42], although all these methods are very straightforward and simple, the differentiation process described here does not require BMP7, FGF2, and RA. With fewer growth factors or small molecules in the differentiation, it is potentially simpler to troubleshoot and adapt to different applications, including generating clinical-grade podocytes for disease modeling and drug screening.

Compared to human primary podocytes, which are non-proliferative in vitro, hPSCs can be used to generate large quantities of healthy or patient-specific human podocytes for disease modeling, drug screening, and development of cell-based therapies. Podocytes have limited capacity for repair or regeneration; thus, podocyte loss is a central feature of many forms of progressive CKD. hPSC-derived podocytes represent an attractive modality to study podocyte injury compared to primary cultures of podocytes which lack proliferation capacity in vitro. In this way, hPSC-derived podocytes could be used to study human glomerular diseases and for screening effects of drugs on glomeruli in vivo. hPSC-derived podocytes also have been shown to reconstitute kidney glomerular-capillary-wall function on a microfluidic chip and this platform may have personalized-medicine applications for diseases due to inherited deficiencies of podocyte genes[32]. hPSC-derived podocytes have been transplanted into mouse kidneys and integrated with glomeruli[33,62], indicating their potential importance in transplantation and kidney regeneration applications. The podocyte differentiation approach reported here utilizes fully defined system and allows the robust generation of podocytes, which can potentially be used for such modeling and cell therapy applications.

Materials and Methods hPSC Culture and Differentiation hPSCs (iPS(IMR90)-4,[60] iPS-DF 19-9-11T,[61] hESCs (H9)[62]) were maintained on Matrigel®-coated (Corning) surfaces in mTeSR®1 (STEMCELL Technologies) as previously described.[63] Before differentiation, hPSCs were singularized with Accutase® (Innovative Cell Technologies) and plated onto (Corning)-coated (or 25 µg/mL Synthemax®, or 5 µg/mL vitronectin (Thermo Fisher)) plates at a density of ~$2 \times 10^4$ cells/cm$^2$ in mTeSR®1 supplemented with 10 µM ROCK inhibitor Y-27632 (Selleckchem). hPSCs were expanded in mTeSR®1 for three days. At day 0, differentiation was initiated by treating cells with 6 µM CHIR99021 (Selleckchem) in podocyte medium 1 (PM1): DMEM/Ham's F12 (Thermo Fisher), 100×MEM nonessential amino acids (Thermo Fisher), 200× GlutaMAX (Thermo Fisher), and 0.1 mM β-mercaptoethanol (Sigma) for 2 days. After 48 hr, medium was changed to podocyte medium 2 (PM2): human Endothelial Serum-Free Medium (hESFM) (Thermo Fisher) supplemented with 50× B-27®. After 4 days of culture in PM2, day 6 cells were dissociated with Accutase® and plated at 1:6 ratio (approximately $4 \times 10^4$ cells/cm$^2$) in PM2 onto 12-well tissue culture plates coated with 100 µg/ml Matrigel® (or 25 µg/mL Synthemax®, or 5 µg/mL vitronectin). At day 10, reaching confluence, cells were split again at the ratio of 1:3. Cells were cultured in PM2 after differentiation day 2 and medium was changed every day for the first 10 days. After day 10, medium was replaced every other day.

Immunochemistry

Cells were rinsed with ice-cold PBS once and fixed with 4% paraformaldehyde (PFA, Electron Microscopy Sciences) for 15 min. Cells were then blocked with 10% goat serum (Thermo Fisher) in PBS (SigmaAldrich) containing 0.3% Triton-X100 (Fisher Scientific) for 30 min (10% PBSGT). Primary antibodies were diluted in 10% PBSGT and cells were incubated in the antibody solutions at 4° C. overnight or at room temperature for 2 hr. After three PBS washes, cells were incubated with secondary antibodies in 10% PBGST (goat anti-rabbit Alexa Fluor 594 (Invitrogen) and goat anti-mouse Alexa Fluor 488 (Invitrogen) 1:200) for 1 hr at room temperature. Cells were then washed with PBS three times followed by treatment with DAPI fluoromount-G (Southern Biotech) and visualized. A list of antibody sources and dilutions is provided in Table 1.

Western Blot Assay

Cells were dissociated with Accutase® and rinsed with PBS twice before being lysed with RIPA (ROCKLAND) in the presence of 1% Halt Protease and Phosphatase Inhibitor Cocktail (Pierce). Protein concentration was determined by a BCA assay kit (Thermo Fisher) according to manufacturer's instructions. Samples containing 30 µg of total protein were loaded onto pre-cast 10% Tris-Glycine SDS/PAGE gels (Invitrogen) under denaturing conditions and transferred to a nitrocellulose membrane. After blocking with 5% non-fat milk in TBST, the membrane was incubated with primary antibody (Table 1) overnight at 4° C. The membrane was then washed, incubated with an anti-mouse/rabbit peroxidase-conjugated secondary antibody (Table 1) for 1 hr at room temperature or overnight at 4° C., and developed by SuperSignal chemiluminescence (Pierce).

Flow Cytometry

Cells were dissociated with Accutase® and fixed in 1% PFA for 15 min at room temperature, then washed with 0.5% BSA (Bio-Rad) plus 0.1% Triton-X100 three times. Cells were stained with primary and secondary antibodies diluted in 0.5% BSA plus 0.1% Triton-X 100 as described.[34] Data were collected on a FACS Caliber flow cytometer (Beckton Dickinson) and analyzed using FlowJo®. Corresponding isotype antibodies were used as FACS gating control. Details about antibody source and usage are provided in Table 1.

TABLE 1

Antibodies used in this study

| Antibody | Vendor | Cat. NO. | Fixation | Dilution | Buffer |
| --- | --- | --- | --- | --- | --- |
| Brachyury | R&D | AF2085 | 4% PFA | 1:200 IF, WB | 1% BSA |
| PAX2 | Santa Cruz | sc-377181 | 4% PFA | 1:200 IF | 10% PBSG |
| WT1 | Santa Cruz | sc-192 | 4% PFA | 1:250 IF, WB | 10% PBSG |
| P-cadherin | Santa Cruz | sc-33635 | 4% PFA | 1:100 IF, WB | 10% PBSG |
| Synaptopodin | Santa Cruz | Sc-50459 | 4% PFA | 1:200 IF, WB | 10% PBSG |
| Podocin | Abcam | Ab50339 | 4% PFA | 1:200 IF, WB | 10% BSA |
| Nephrin | Abcam | Ab72908 | 4% PFA | 1:500 WB | 5% milk |
| CD2AP | Santa Cruz | SC-9137 | 4% PFA | 1:100 IF | 10% PBSG |
| SIX2 | Proteintech | 11562-1-AP | 4% PFA | 1:200 IF | 10% PBSG |
| ZO-1 | Invitrogen | 402200 | 4% PFA | 1:200 IF | 10% PBSG |
| Ki67 | BD | 550609 | 4% PFA | 1:100 IF | 10% PBSG |
| OCT3/4 | Santa Cruz | sc-5279 | 4% PFA | 1:100 IF | 10% PBSG |
| TRA-1-60 | Santa Cruz | sc-21705 | 4% PFA | 1:100 IF | 10% PBSG |
| NANOG | Santa Cruz | sc-374001 | 4% PFA | 1:100 IF | 10% PBSG |
| β-actin | Cell signaling | 5125s | | 1:2000 WB | 5% milk |

TABLE 1-continued

Antibodies used in this study

| Antibody | Vendor | Cat. NO. | Fixation | Dilution | Buffer |
|---|---|---|---|---|---|
| P-SMAD | Cell signaling | 13820 | | 1:1000 WB | 5% BSA |
| SMAD | Cell signaling | 6944 | | 1:1000 WB | 5% milk |
| BMP7 | Abcam | Ab54904 | 4% PFA | 1:100 IF | 10% PBSG |

Quantitative RT-PCR

Total RNA was extracted with the RNeasy® mini kit (QIAGEN) and treated with DNase (QIAGEN). 1 µg total RNA was reverse transcribed into cDNA using Oligo (dT) primer with Superscript™ III Reverse Transcriptase (Invitrogen). Real-time quantitative PCR was done in triplicate with iQTMSYBR® Green SuperMix (Bio-Rad). GAPDH was used as an endogenous housekeeping control. Primer sequences are provided in Table 2.

TABLE 2 qPCR primers used in this study.

| Gene name | | Primer length | Product length |
|---|---|---|---|
| GAPDH | | | 207 |
| Forward | CTGATTTGGTCGTATTGGGC (SEQ ID NO: 1) | 20 | |
| Reverse | TGGAAGATGGTGATGGGATT (SEQ ID NO: 2) | 20 | |
| POU5F1 | | | 120 |
| Forward | GTGGAGGAAGCTGACAACAA (SEQ ID NO: 3) | 20 | |
| Reverse | ATTCTCCAGGTTGCCTCTCA (SEQ ID NO: 4) | 20 | |
| MIXL1 | | | 130 |
| Forward | GGCGTCAGAGTGGGAAATCC (SEQ ID NO: 5) | 20 | |
| Reverse | GGCAGGCAGTTCACATCTACC (SEQ ID NO: 6) | 21 | |
| PAX2 | | | 92 |
| Forward | TCAAGTCGAGTCTATCTGCATCC (SEQ ID NO: 7) | 23 | |
| Reverse | CATGTCACGACCAGTCACAAC (SEQ ID NO: 8) | 21 | |
| WT1 | | | 142 |
| Forward | TCGGCTTACGGGTCGTTG (SEQ ID NO: 9) | 18 | |
| Reverse | TGAAGGCGCTCAGGCACT (SEQ ID NO: 10) | 18 | |
| SIX2 | | | 247 |
| Forward | AGCGGCAAGTCGGTGTTAG (SEQ ID NO: 11) | 19 | |
| Reverse | GGTTGGCTGACATGGGGTT (SEQ ID NO: 12) | 19 | |
| TJP1 | | | 128 |
| Forward | ACCAGTAAGTCGTCCTGATCC (SEQ ID NO: 13) | 21 | |
| Reverse | TCGGCCAAATCTTCTCACTCC (SEQ ID NO: 14) | 21 | |
| CDH3 | | | 121 |
| Forward | TGGAGATCCTTGATGCCAATGA (SEQ ID NO: 15) | 22 | |
| Reverse | GCGTCCAGATCAGTGACCG (SEQ ID NO: 16) | 19 | |
| SYNPO | | | 89 |
| Forward | CCGCAAATCCATGTTTACTT (SEQ ID NO: 17) | 20 | |
| Reverse | GCTTCTCATCCGCTGTCTGT (SEQ ID NO: 18) | 20 | |

Albumin Uptake Assay

Differentiated podocytes at day 16 were incubated with the Alexa Fluor™ 555 conjugated albumin (Thermo Fisher) at 500 µg/mL for 1 hr at 37° C. The cells incubated with same concentration of albumin at 4° C. were used as a control. The cells were then rinsed with ice-cold PBS three times and fixed with 4% PFA. Nuclei were counterstained with DAPI and visualized.

Contractility Assay and Apoptosis Assay

Differentiated podocytes at day 16 were treated with 500 ng/ml Ang II for 6 hr or 2 ng/ml TGF-β1 for 24 hr. After 6 hr, the cells treated with Ang II were fixed with 4% PFA and stained with DyLight® conjugated phalloidin (Thermo Fisher). Nuclei were counterstained with DAPI and visualized. The cells treated with TGF-β1 after 24 hr were assessed by counting dead cells with trypan blue exclusion.

Statistics

Data are presented as mean±standard error of the mean (SEM). Statistical significance was determined by Student's t-test (two-tail) between two groups. P<0.05 was considered statistically different.

Figure 12:
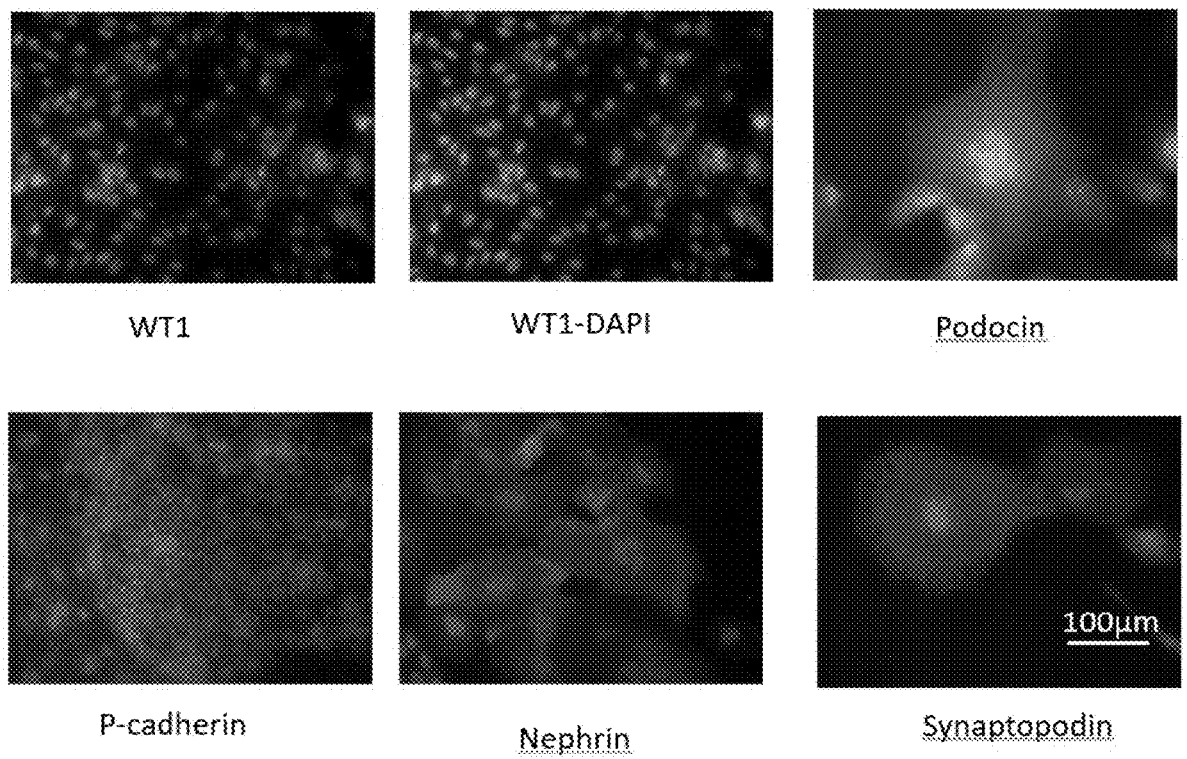
FIG. 12. Maintenance of podocyte phenotype in culture. iPSC-derived podocytes differentiated as illustrated in FIG. 1A were able to be expanded and maintained in culture for over 30 days, exhibiting expression of podocyte markers as shown by immunofluorescence.

Example 2: Podocytes Proliferate and are Maintained in Culture for Extended Time Podocytes were maintained and passaged in culture as described in Example 1. As demonstrated in FIG. 12, podocytes maintained their podocyte characteristics (e.g., positive expression for podocin, P-cadherin, nephrin and synaptopodin) for at least for 30 days in culture as shown by surface staining. Podocytes were able to be maintained in culture for up to 60 days (data not shown).

REFERENCE

1. Pavenstädt, H., Kriz, W. & Kretzler, M. Cell biology of the glomerular podocyte. *Physiological reviews* 83, 253-307 (2003).
2. Schwarz, K. et al. Podocin, a raft-associated component of the glomerular slit diaphragm, interacts with CD2AP and nephrin. *The Journal of clinical investigation* 108, 1621-1629 (2001).
3. Ryan, G. B. & Karnovsky, M. J. Distribution of endogenous albumin in the rat glomerulus: role of hemodynamic factors in glomerular barrier function. *Kidney international* 9, 36-45 (1976).
4. Haraldsson, B., Nyström, J. & Deen, W. M. Properties of the glomerular barrier and mechanisms of proteinuria. *Physiological reviews* 88, 451-487 (2008).
5. Nangaku, M. Chronic hypoxia and tubulointerstitial injury: a final common pathway to end-stage renal failure. *Journal of the American Society of Nephrology* 17, 17-25 (2006).
6. Boute, N. et al. NPHS2, encoding the glomerular protein podocin, is mutated in autosomal recessive steroid-resistant nephrotic syndrome. *Nature genetics* 24, 349-354 (2000).
7. Foley, R. N., Parfrey, P. S. & Sarnak, M. J. Clinical epidemiology of cardiovascular disease in chronic renal disease. *American Journal of Kidney Diseases* 32, S112-S119 (1998).
8. Koffler, D., Schur, P. H. & Kunkel, H. G. Immunological studies concerning the nephritis of systemic lupus erythematosus. *Journal of Experimental Medicine* 126, 607-624 (1967).
9. Wilson, C. B. & Smith, R. C. Goodpasture's syndrome associated with influenza A2 virus infection. *Ann Intern Med* 76, 91-94 (1972).
10. Radford, M. G., Donadio, J. V., Bergstralh, E. J. & Grande, J. P. Predicting renal outcome in IgA nephropathy. *Journal of the American Society of Nephrology* 8, 199-207 (1997).
11. Neugarten, J. & Baldwin, D. S. Glomerulonephritis in bacterial endocarditis. *The American journal of medicine* 77, 297-304 (1984).
12. BARISONI, L., Kriz, W., Mundel, P. & D'AGATI, V. The Dysregulated Podocyte Phenotype A Novel Concept in the Pathogenesis of Collapsing Idiopathic Focal Segmental Glomerulosclerosis and HIV-Associated Nephropathy. *Journal of the American Society of Nephrology* 10, 51-61 (1999).
13. Kashtan, C. E. Alport syndrome and thin glomerular basement membrane disease. *Journal of the American Society of Nephrology* 9, 1736-1750 (1998).
14. Sassy-Prigent, C. et al. Early glomerular macrophage recruitment in streptozotocin-induced diabetic rats. *Diabetes* 49, 466-475 (2000).
15. Baylis, C., Mitruka, B. & Deng, A. Chronic blockade of nitric oxide synthesis in the rat produces systemic hypertension and glomerular damage. *Journal of Clinical Investigation* 90, 278 (1992).
16. Schieppati, A. & Remuzzi, G. Chronic renal diseases as a public health problem: epidemiology, social, and economic implications. *Kidney International* 68, S7-S10 (2005).
17. Couser, W. G., Remuzzi, G., Mendis, S. & Tonelli, M. The contribution of chronic kidney disease to the global burden of major noncommunicable diseases. *Kidney international* 80, 1258-1270 (2011).
18. Saleem, M. A. et al. A conditionally immortalized human podocyte cell line demonstrating nephrin and podocin expression. *Journal of the American Society of Nephrology* 13, 630-638 (2002).
19. Susztak, K., Raff, A. C., Schiffer, M. & Böttinger, E. P. Glucose-induced reactive oxygen species cause apoptosis of podocytes and podocyte depletion at the onset of diabetic nephropathy. *Diabetes* 55, 225-233 (2006).
20. Durvasula, R. V. et al. Activation of a local tissue angiotensin system in podocytes by mechanical strain. *Kidney international* 65, 30-39 (2004).
21. Dunn, K., Aotaki-Keen, A., Putkey, F. & Hjelmeland, L. M. ARPE-19, a human retinal pigment epithelial cell line with differentiated properties. *Experimental eye research* 62, 155-170 (1996).
22. Pavenstädt, H. Roles of the podocyte in glomerular function. *American Journal of Physiology-Renal Physiology* 278, F173-F179 (2000).
23. Wharram, B. L. et al. Podocyte depletion causes glomerulosclerosis: Diphtheria toxin-induced podocyte depletion in rats expressing human diphtheria toxin receptor transgene. *Journal of the American Society of Nephrology* 16, 2941-2952 (2005).
24. Mundel, P. et al. Rearrangements of the cytoskeleton and cell contacts induce process formation during differentiation of conditionally immortalized mouse podocyte cell lines. *Experimental cell research* 236, 248-258 (1997).
25. Chittiprol, S., Chen, P., Petrovic-Djergovic, D., Eichler, T. & Ransom, R. F. Marker expression, behaviors, and responses vary in different lines of conditionally immortalized cultured podocytes. *American Journal of Physiology-Renal Physiology* 301, F660-F671 (2011).

26. Takasato, M. et al. Directing human embryonic stem cell differentiation towards a renal lineage generates a self-organizing kidney. *Nature cell biology* 16, 118-126 (2014).
27. Xia, Y. et al. Directed differentiation of human pluripotent cells to ureteric bud kidney progenitor-like cells. *Nature cell biology* 15, 1507-1515 (2013).
28. Takasato, M. et al. Kidney organoids from human iPS cells contain multiple lineages and model human nephrogenesis. *Nature* 526, 564-568 (2015).
29. Song, B. et al. The directed differentiation of human iPS cells into kidney podocytes. *PloS one* 7, e46453 (2012).
30. Musah, S. et al. Mature induced-pluripotent-stem-cell-derived human podocytes reconstitute kidney glomerular-capillary-wall function on a chip. *Nature Biomedical Engineering* 1, 0069 (2017).
31. Mae, S.-I. et al. Monitoring and robust induction of nephrogenic intermediate mesoderm from human pluripotent stem cells. *Nature communications* 4, 1367 (2013).
32. Perantoni, A. O. in Seminars in cell & developmental biology, Vol. 14 201-208 (Elsevier, 2003).
33. Marcelle, C., Stark, M. R. & Bronner-Fraser, M. Coordinate actions of BMPs, Wnts, Shh and noggin mediate patterning of the dorsal somite. *Development* 124, 3955-3963 (1997).
34. Lian, X. et al. Robust cardiomyocyte differentiation from human pluripotent stem cells via temporal modulation of canonical Wnt signaling. *Proceedings of the National Academy of Sciences* 109, E1848-E1857 (2012).
35. Lian, X. et al. Chemically defined, albumin-free human cardiomyocyte generation. *Nature methods* 12, 595-596 (2015).
36. Kreidberg, J. A. WT1 and kidney progenitor cells. *Organogenesis* 6, 61-70 (2010).
37. Obara-Ishihara, T., Kuhlman, J., Niswander, L. & Herzlinger, D. The surface ectoderm is essential for nephric duct formation in intermediate mesoderm. *Development* 126, 1103-1108 (1999).
38. Ciampi, O. et al. Generation of functional podocytes from human induced pluripotent stem cells. *Stem cell research* 17, 130-139 (2016).
39. Xia, Y. et al. The generation of kidney organoids by differentiation of human pluripotent cells to ureteric bud progenitor-like cells. *Nature protocols* 9, 2693-2704 (2014).
40. Mendelsohn, C. et al. Function of the retinoic acid receptors (RARs) during development (II). Multiple abnormalities at various stages of organogenesis in RAR double mutants. *Development* 120, 2749-2771 (1994).
41. Duester, G. Retinoic acid synthesis and signaling during early organogenesis. *Cell* 134, 921-931 (2008).
42. Burrow, C. R. Regulatory molecules in kidney development. *Pediatric nephrology* 14, 240-253 (2000).
43. Kuroda, K., Kuang, S., Taketo, M. M. & Rudnicki, M. A. Canonical Wnt signaling induces BMP-4 to specify slow myofibrogenesis of fetal myoblasts. *Skeletal muscle* 3, 5 (2013).
44. Vieira, A. F. & Paredes, J. P-cadherin and the journey to cancer metastasis. *Molecular cancer* 14, 178 (2015).
45. Chen, H.-F. et al. Surface marker epithelial cell adhesion molecule and E-cadherin facilitate the identification and selection of induced pluripotent stem cells. *Stem Cell Reviews and Reports* 7, 722-735 (2011).
46. Yanagida-Asanuma, E. et al. Synaptopodin protects against proteinuria by disrupting Cdc42: IRSp53: Mena signaling complexes in kidney podocytes. *The American journal of pathology* 171, 415-427 (2007).
47. Ruotsalainen, V. et al. Nephrin is specifically located at the slit diaphragm of glomerular podocytes. *Proceedings of the National Academy of Sciences* 96, 7962-7967 (1999).
48. Shankland, S., Pippin, J., Reiser, J. & Mundel, P. Podocytes in culture: past, present, and future. *Kidney international* 72, 26-36 (2007).
49. Xinaris, C. et al. Functional human podocytes generated in organoids from amniotic fluid stem cells. *Journal of the American Society of Nephrology, ASN.* 2015030316 (2015).
50. Carson, J. M. et al. Podocytes degrade endocytosed albumin primarily in lysosomes. *PLoS One* 9, e99771 (2014).
51. Kriz, W. et al. A role for podocytes to counteract capillary wall distension. *Kidney international* 45, 369-376 (1994).
52. Schiffer, M. et al. Apoptosis in podocytes induced by TGF-β and Smad7. *The Journal of clinical investigation* 108, 807-816 (2001).
53. Das, R. et al. Transforming growth factor β1-induced apoptosis in podocytes via the extracellular signal-regulated kinase-mammalian target of rapamycin complex 1-NADPH oxidase 4 axis. *Journal of Biological Chemistry* 290, 30830-30842 (2015).
54. Griffin, S. V., Petermann, A. T., Durvasula, R. V. & Shankland, S. J. Podocyte proliferation and differentiation in glomerular disease: role of cell-cycle regulatory proteins. *Nephrology Dialysis Transplantation* 18, vi8-vi13 (2003).
55. Kirouac, D. C. & Zandstra, P. W. The systematic production of cells for cell therapies. *Cell stem cell* 3, 369-381 (2008).
56. Serra, M., Brito, C., Correia, C. & Alves, P. M. Process engineering of human pluripotent stem cells for clinical application. *Trends in biotechnology* 30, 350-359 (2012).
57. Cho, Y. D. et al. Wnt3a stimulates Mepe, Matrix extracellular phosphoglycoprotein, expression directly by the activation of the canonical Wnt signaling pathway and indirectly through the stimulation of autocrine Bmp-2 expression. *Journal of cellular physiology* 227, 2287-2296 (2012).
58. Sharmin, S. et al. Human induced pluripotent stem cell-derived podocytes mature into vascularized glomeruli upon experimental transplantation. *Journal of the American Society of Nephrology, ASN.* 2015010096 (2015).
59. Musah, S. et al. Mature induced-pluripotent-stem-cell-derived human podocytes reconstitute kidney glomerular-capillary-wall function on a chip. *Nature Biomedical Engineering* 1, s41551-41017-40069 (2017).
60. Yu, J. et al. Induced pluripotent stem cell lines derived from human somatic cells. *Science* 318, 1917-1920 (2007).
61. Yu, J. et al. Human induced pluripotent stem cells free of vector and transgene sequences. *Science* 324, 797-801 (2009).
62. Thomson, J. A. et al. Embryonic stem cell lines derived from human blastocysts. *Science* 282, 1145-1147 (1998).
63. Ludwig, T. E. et al. Feeder-independent culture of human embryonic stem cells. *Nature methods* 3, 637-646 (2006).

Each publication, patent, and patent publication cited in this disclosure is incorporated in reference herein in its entirety. The present invention is not intended to be limited to the foregoing examples, but encompasses all such modifications and variations as come within the scope of the appended claims.

The invention claimed is:

1. A method of producing nephron progenitor cells, the method comprising:
   a) culturing a human induced pluripotent stem cells (iPSC) population for about three days;
   b) validating the expression of OCT4, NANOG, and TRA-1-60 in the iPSC;
   c) differentiating the iPSC in serum-free and albumin-free medium containing DMEM/F12, 1% MEM-NEAA, 2-6 mM L-alanyl-L-glutamine dipeptide, GlutaMAX, and 0.1mM (β-mercaptoethanol; and a GSK3 inhibitor;
   c. confirming the expression of a Brachyury$^+$ primitive streak cell population-48 hours after differentiating the iPSC;
   d. differentiating the Brachyury$^+$ primitive streak cell population in human endothelial serum-free and human albumin-free medium, free of exogenous Wnt/β-catenin activating agent, bone morphogenetic proteins (BMPs), Activin, retinoic acid (RA), vascular endothelial growth factor (VEGF) and fibroblast growth factor (FGF) but comprising biotin, DL alpha tocopherol acetate, DL alpha-tocopherol, vitamin A, BSA, fatty acid free fraction V, catalase, human recombinant insulin, human transferrin, superoxide dismutase, corticosterone, D-galactose, ethanolamine HCl, glutathione, L-carnitine, L-carnitine HCl, linoleic acid, linolenic acid, progesterone, putrescine 2HCl, sodium selenite and T3 (triodo-I-thyronine) for a time sufficient to differentiate a portion of the cultured cells into PAX2$^+$ WT1$^+$ SIX2$^+$ nephron progenitor cells.

2. The method of claim 1, wherein at least 75% of the differentiated cells are PAX2$^+$ WT1$^+$ SIX2$^+$ nephron progenitor cells.

3. The method of claim 2, wherein at least 90% of the differentiated cells are PAX2$^+$ WT1$^+$ SIX2$^+$ nephron progenitor cells.

4. The method of claim 3, wherein at least 95% of the differentiated cells are PAX2$^+$ WT1$^+$ SIX2$^+$ nephron progenitor cells.

5. The method of claim 1, wherein the sufficient time is at least 4 days.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
ctgatttggt cgtattgggc					20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
tggaagatgg tgatgggatt					20

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
gtggaggaag ctgacaacaa					20

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
attctccagg ttgcctctca					20

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
ggcgtcagag tgggaaatcc					20

<210> SEQ ID NO 6
<211> LENGTH: 21
<212> TYPE: DNA
<213> ORGANISM: Artificial Sequence
<220> FEATURE:
<223> OTHER INFORMATION: synthetic

<400> SEQUENCE: 6
ggcaggcagt tcacatctac c					21

<210> SEQ ID NO 7
<211> LENGTH: 23
<212> TYPE: DNA
<213> ORGANISM: Artificial Sequence

```
<220> FEATURE:
<223> OTHER INFORMATION: synthetic

<400> SEQUENCE: 7
tcaagtcgag tctatctgca tcc                                              23

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
catgtcacga ccagtcacaa c                                                21

<210> SEQ ID NO 9
<211> LENGTH: 18
<212> TYPE: DNA
<213> ORGANISM: Artificial Sequence
<220> FEATURE:
<223> OTHER INFORMATION: synthetic

<400> SEQUENCE: 9
tcggcttacg ggtcgttg                                                    18

<210> SEQ ID NO 10
<211> LENGTH: 18
<212> TYPE: DNA
<213> ORGANISM: Artificial Sequence
<220> FEATURE:
<223> OTHER INFORMATION: synthetic

<400> SEQUENCE: 10
tgaaggcgct caggcact                                                    18

<210> SEQ ID NO 11
<211> LENGTH: 19
<212> TYPE: DNA
<213> ORGANISM: Artificial Sequence
<220> FEATURE:
<223> OTHER INFORMATION: synthetic

<400> SEQUENCE: 11
agcggcaagt cggtgttag                                                   19

<210> SEQ ID NO 12
<211> LENGTH: 19
<212> TYPE: DNA
<213> ORGANISM: Artificial Sequence
<220> FEATURE:
<223> OTHER INFORMATION: synthetic

<400> SEQUENCE: 12
ggttggctga catggggtt                                                   19

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
accagtaagt cgtcctgatc c                                                21
```

```
<210> SEQ ID NO 14
<211> LENGTH: 21
<212> TYPE: DNA
<213> ORGANISM: Artificial Sequence
<220> FEATURE:
<223> OTHER INFORMATION: synthetic

<400> SEQUENCE: 14
tcggccaaat cttctcactc c                                         21

<210> SEQ ID NO 15
<211> LENGTH: 22
<212> TYPE: DNA
<213> ORGANISM: Artificial Sequence
<220> FEATURE:
<223> OTHER INFORMATION: synthetic

<400> SEQUENCE: 15
tggagatcct tgatgccaat ga                                        22

<210> SEQ ID NO 16
<211> LENGTH: 19
<212> TYPE: DNA
<213> ORGANISM: Artificial Sequence
<220> FEATURE:
<223> OTHER INFORMATION: synthetic

<400> SEQUENCE: 16
gcgtccagat cagtgaccg                                            19

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
ccgcaaatcc atgtttactt                                           20

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
gcttctcatc cgctgtctgt                                           20
```